US010413881B2

(12) United States Patent
Kshirsagar et al.

(10) Patent No.: US 10,413,881 B2
(45) Date of Patent: *Sep. 17, 2019

(54) POROUS ARTICLES FOR SEPARATION

(71) Applicant: 3M INNOVATIVE PROPERTIES COMPANY, St. Paul, MN (US)

(72) Inventors: Manjiri T. Kshirsagar, Woodbury, MN (US); Hassan Sahouani, Hastings, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 313 days.

This patent is subject to a terminal disclaimer.

(21) Appl. No.: 15/039,664

(22) PCT Filed: Dec. 16, 2014

(86) PCT No.: PCT/US2014/070448
§ 371 (c)(1),
(2) Date: May 26, 2016

(87) PCT Pub. No.: WO2015/095100
PCT Pub. Date: Jun. 25, 2015

(65) Prior Publication Data
US 2017/0157591 A1  Jun. 8, 2017

Related U.S. Application Data

(60) Provisional application No. 61/917,517, filed on Dec. 18, 2013.

(51) Int. Cl.
*B01D 15/00* (2006.01)
*B01J 20/26* (2006.01)
(Continued)

(52) U.S. Cl.
CPC ............ *B01J 20/261* (2013.01); *B01D 15/00* (2013.01); *B01J 20/267* (2013.01);
(Continued)

(58) Field of Classification Search
CPC ....... B01D 15/00; B01J 20/261; B01J 20/267; B01J 20/28028; B01J 20/3064;
(Continued)

(56) References Cited

U.S. PATENT DOCUMENTS 6,048,908 A  4/2000  Kitagawa
6,180,010 B1  1/2001  Alper
(Continued)

FOREIGN PATENT DOCUMENTS

WO  WO 2006/115486  11/2006
WO  WO 2006/133519  12/2006
(Continued)

OTHER PUBLICATIONS

Herbert, Thomas J., "Membranes: Cell Membrane Structure," (2010), downloaded from miami.edu Feb. 2019 (Year: 2010).*
(Continued)

*Primary Examiner* — Lucas A Stelling
(74) *Attorney, Agent, or Firm* — Jean A. Lown

(57) ABSTRACT

Porous articles are provided that include a fibrous porous matrix and porous polymeric particles. The porous polymeric particles are distributed throughout the fibrous porous polymeric matrix. The porous article can be used to prepare a separation device or a system that includes the separation device. The porous articles can be used for the separation of a target material such as a microorganism (i.e., cellular analyte) from a sample.

19 Claims, 2 Drawing Sheets

(51) Int. Cl.
*B01J 20/28* (2006.01)
*B01J 20/30* (2006.01)
*C08F 2/44* (2006.01)
*C08J 9/16* (2006.01)
*C08J 9/26* (2006.01)
*C08J 9/28* (2006.01)
*C08F 220/12* (2006.01)
*C08F 220/18* (2006.01)
*C12Q 1/10* (2006.01)

(52) U.S. Cl.
CPC ..... *B01J 20/28028* (2013.01); *B01J 20/3064* (2013.01); *C08F 2/44* (2013.01); *C08F 220/12* (2013.01); *C08F 220/18* (2013.01); *C08J 9/16* (2013.01); *C08J 9/26* (2013.01); *C08J 9/286* (2013.01); *C12Q 1/10* (2013.01); *C08J 2201/0462* (2013.01); *C08J 2333/06* (2013.01); *C08J 2333/14* (2013.01)

(58) Field of Classification Search
CPC ........ C08F 2/44; C08F 220/12; C08F 220/18; C08J 9/16; C08J 9/26; C08J 9/286; C08J 2201/0462; C08J 2333/06; C08J 2333/14; C12Q 1/10
See application file for complete search history.

(56) References Cited

U.S. PATENT DOCUMENTS

| 6,451,260 | B1 | 9/2002 | Düsterhöft |
| 7,422,868 | B2 | 9/2008 | Fan |
| 2007/0154703 | A1 | 7/2007 | Waller |
| 2007/0256981 | A1 | 11/2007 | Krogue |
| 2010/0104647 | A1 | 4/2010 | Ting |
| 2010/0311850 | A1* | 12/2010 | Wickert ................ B01D 15/08 521/61 |
| 2010/0323573 | A1 | 12/2010 | Chu |
| 2011/0123456 | A1 | 5/2011 | Pandit |
| 2013/0244225 | A1 | 9/2013 | Kshirsagar |
| 2013/0260370 | A1 | 10/2013 | Kshirsagar |
| 2016/0115430 | A1 | 4/2016 | Swanson |

FOREIGN PATENT DOCUMENTS

| WO | WO 2007/075442 | 7/2007 | |
| WO | WO 2007/075508 | 7/2007 | |
| WO | WO 2009/061759 | 5/2009 | |
| WO | WO 2009/085424 | 7/2009 | |
| WO | Wo 2011/156255 | 12/2011 | |
| WO | WO-2012078374 A2 * | 6/2012 | ............ C12M 47/02 |
| WO | WO 2013/077981 | 5/2013 | |
| WO | WO 2013/184373 | 12/2013 | |
| WO | WO 2014/186328 | 11/2014 | |

OTHER PUBLICATIONS

International Search Report for PCT International Application No. PCT/US2014/070448, dated Apr. 28, 2015, 4 pages.

* cited by examiner

POROUS ARTICLES FOR SEPARATION

CROSS REFERENCE TO RELATED APPLICATIONS

This application is a national stage filing under 35 U.S.C. 371 of PCT/US2014/070448, filed Dec. 16, 2014, which claims the benefit of U.S. Provisional Application No. 61/917,517, filed Dec. 18, 2013, the disclosure of which is incorporated by reference in its/their entirety herein.

FIELD

Porous articles, methods of making the porous articles, separation devices containing the porous articles, and systems containing the separation devices are provided.

BACKGROUND

Infections resulting from microorganism contamination are a growing concern worldwide. Thus, it is desirable or necessary to analyze various clinical, food, environmental, or other samples to identify and/or quantify microorganisms that may be present. The microorganisms often need to be separated from at least some of the other components in samples or concentrated prior to identification and/or quantification. Additionally, it may be desirable or necessary to purify various materials such as fluid samples by removing various microorganisms.

Many of the materials that have been used for the separation or removal of microorganisms have been inorganic materials. Such materials are described, for example, in Patent Application Publications WO 2006/133519 A1 (Finnie et al.), WO 2012/078426 (Kshirsagar et al.), and WO 2012/078374 (Kshirsagar et al.).

Various polymeric particles having pores have been prepared. Some of these have been used, for example, as ion exchange resins or other chromatographic resins. Others have been used, for example, to adsorb and/or deliver different active agents. Such particles are described, for example, in U.S. Patent Application 2010/0104647 (Ting), U.S. Patent Application Publication 2011/0123456 (Pandit et al.), U.S. Pat. No. 6,048,908 (Kitagawa), and Patent Application Publications WO 2013/077981 (Sahouani), WO 2007/075508 (Rasmussen et al.), and WO 2007/075442 (Rasmussen et al.).

SUMMARY

Porous articles are provided that include a fibrous porous matrix and porous polymeric particles distributed throughout the fibrous porous matrix. The porous article can be used in a separation device or in a system that includes the separation device. The porous articles can be used for the separation of a target material such as a microorganism (i.e., cellular analyte) from a sample. More particularly, the target material can be bound or captured by the porous article.

In a first aspect, a porous article is provided. The porous article includes a) porous polymeric particles and b) a fibrous porous matrix, wherein the porous polymeric particles are distributed throughout the fibrous porous matrix. The porous polymeric particles include a polymerized product of a reaction mixture that contains i) a monomer composition and ii) a poly(propylene glycol) having a weight average molecular weight of at least 500 grams/mole. The monomer composition contains at least 10 weight percent of a first monomer of Formula (I)

$$CH_2=C(R^1)-(CO)-O[-CH_2-CH_2-O]_p-(CO)-C(R^1)=CH_2 \quad (I)$$

based on a total weight of the monomer composition. In Formula (I), the variable p is an integer equal to at least 1 and $R^1$ is hydrogen or alkyl. The poly(propylene glycol) is removed from the polymerized product to provide the porous polymeric particles.

In one embodiment of the first aspect, the reaction mixture used to form the porous polymeric particles includes (a) a first phase and (b) a second phase dispersed in the first phase, wherein a volume of the first phase is greater than a volume of the second phase. The first phase contains (i) a compound of Formula (II)

$$HO[-CH_2-CH(OH)-CH_2-O]_n-H \quad (II)$$

where the variable n is an integer equal to at least 1 and (ii) a nonionic surfactant. The second phase contains (i) a monomer composition containing at least 10 weight percent of the first monomer of Formula (I)

$$CH_2=C(R^1)-(CO)-O[-CH_2-CH_2-O]_p-(CO)-C(R^1)=CH_2 \quad (I)$$

based on the total weight of the monomer composition and (ii) the poly(propylene glycol) having a weight average molecular weight of at least 500 grams/mole. In Formula (I), the variable p is an integer equal to at least 1 and the group $R^1$ is hydrogen or methyl.

In a second aspect, a method of making a porous article is provided. The method includes a) providing a plurality of porous polymeric particles and b) distributing the porous polymeric particles throughout a fibrous porous matrix. The porous polymeric particles include a polymerized product of a reaction mixture that contains i) a monomer composition and ii) a poly(propylene glycol) having a weight average molecular weight of at least 500 grams/mole. The monomer composition contains at least 10 weight percent of a first monomer of Formula (I)

$$CH_2=C(R^1)-(CO)-O[-CH_2-CH_2-O]_p-(CO)-C(R^1)=CH_2 \quad (I)$$

based on a total weight of the monomer composition. In Formula (I), the variable p is an integer equal to at least 1 and $R^1$ is hydrogen or alkyl. The poly(propylene glycol) is removed from the polymerized product to provide the porous polymeric particles.

In a third aspect, a separation device is provided. The separation device includes a) a container having an inlet and an outlet for passage of a fluid stream through the container and b) a porous article positioned within the container. The porous article is the same as described above.

In a fourth aspect, a system is provided. The system includes a separation device that includes a) a container having an inlet and an outlet and b) a porous article positioned within the container. The porous article is the same as described above. The system further includes a fluid stream passing through the separation device, wherein the fluid stream enters the inlet and exits the outlet of the container and contacts the porous article positioned within the container.

In a fifth aspect, a method of separating a target material is provided. The method includes providing a separation device. The separation device includes a container having an inlet and an outlet. The porous article is the same as described above. The method further includes passing a fluid stream comprising a target material through the separation device, wherein the fluid stream enters the inlet and exits the outlet of the container and contacts the porous article positioned within the container. The method still further includes removing the target material from the fluid stream, wherein the target material is bound or captured by the porous article. In some embodiments of the fifth aspect, the target material is a microorganism.

DETAILED DESCRIPTION

Figure 1:
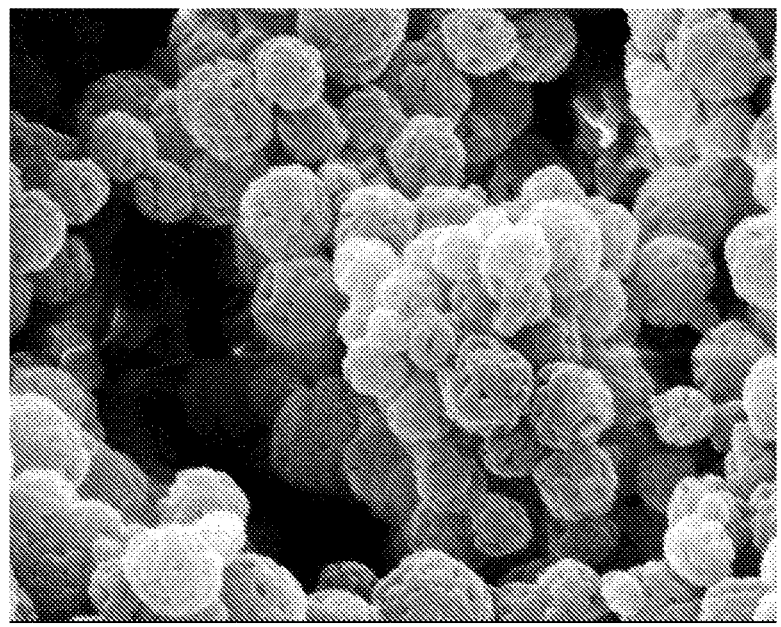
FIG. 1 is the scanning electron micrograph (SEM) of porous polymeric particles prepared as described in Preparatory Example 1.
Figure 2:
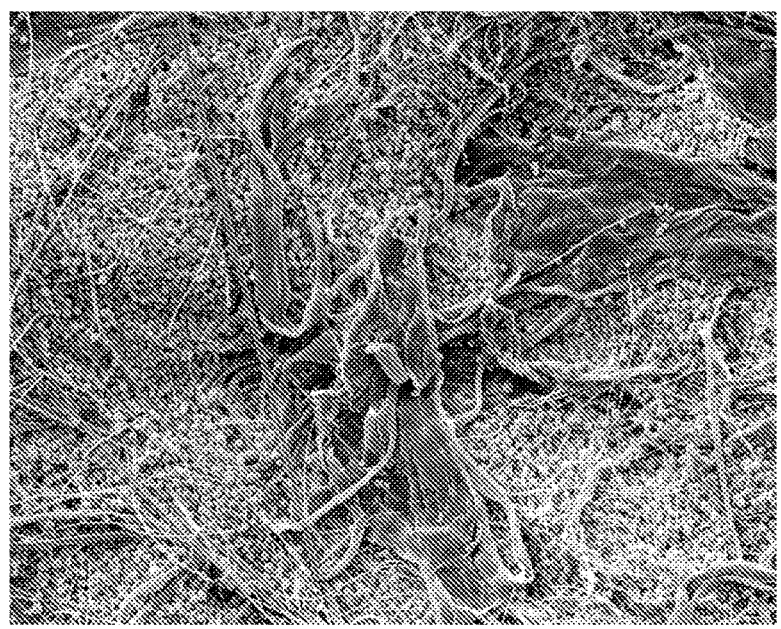
FIG. 2 and FIG. 3 are scanning electron micrographs of the porous article of Example 1 at two different magnifications.
Figure 3:
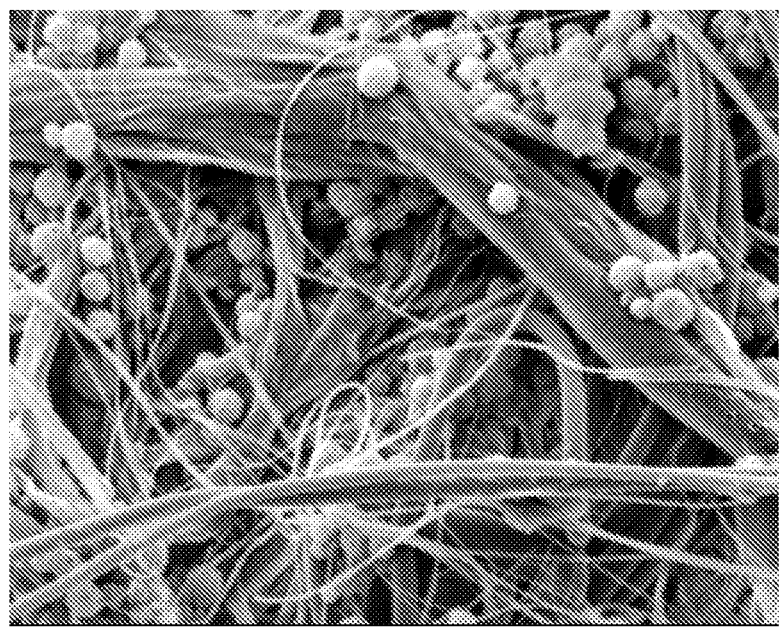

Porous articles are provided that include a fibrous porous matrix and porous polymeric particles distributed throughout the fibrous porous matrix. The porous article can be used to prepare a separation device or a system that includes the separation device. The porous articles can be used for the separation of a target material such as a microorganism (i.e., cellular analyte) from a sample.

Both the porous polymeric particles and the fibrous porous matrix have voids or free volume. The voids in the fibrous porous matrix allow a fluid stream to flow through or over the porous article and contact the porous polymeric particles distributed throughout the fibrous porous matrix. The porous polymeric particles have pores on its outer surface and, at least in some embodiments, can have hollow interiors. The terms "porous polymeric particle" and "polymeric particle" are used interchangeably.

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like.

The term "a", "an", and "the" are used interchangeably with "at least one" to mean one or more of the elements being described.

The term "and/or" means either or both. For example "A and/or B" means only A, only B, or both A and B.

The term "monomer composition" refers to that portion of a polymerizable composition that includes the monomers and only the monomers. More specifically, the monomer composition includes at least the first monomer of Formula (I). The term "reaction mixture" includes, for example, the monomer composition, the poly(propylene glycol), any other components such as those included in the first phase and the second phase described below. Some of the components in the reaction mixture but may not undergo a chemical reaction but can influence the chemical reaction and the resulting polymeric material.

In a first aspect, a porous article is provided. The porous article includes a) porous polymeric particles and b) a fibrous porous matrix, wherein the porous polymeric particles are distributed throughout the fibrous porous matrix. The porous polymeric particles include a polymerized product of a reaction mixture that that contains i) a monomer composition and ii) a poly(propylene glycol) having a weight average molecular weight of at least 500 grams/mole. The monomer composition contains at least 10 weight percent of a first monomer of Formula (I)

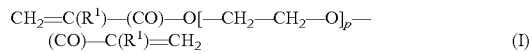

(I)

based on a total weight of the monomer composition. In Formula (I), the variable p is an integer equal to at least 1 and $R^1$ is hydrogen or alkyl.

The variable p in Formula (I) is an integer no greater than 30, no greater than 20, no greater than 16, no greater than 12, or no greater than 10. The number average molecular weight of the ethylene oxide portion of the monomer (i.e., the group —[CH$_2$CH$_2$—O]$_p$—) is often no greater than 1200 grams/mole, no greater 1000 grams/mole, no greater than 800 grams/mole, no greater than 1000 grams, mole, no greater than 600 grams/mole, no greater than 400 grams/mole, no greater than 200 grams/mole, or no greater than 100 grams/mole. The group $R^1$ in Formula (I) is hydrogen or methyl.

Suitable first monomers of Formula (I) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, and SR740 for polyethylene glycol (1000) dimethacrylate.

The reaction mixture used to form the porous polymeric particles also includes a poly(propylene glycol) having a weight average molecular weight of at least 500 grams/mole. The polypropylene glycol functions as a porogen that gets partially entrained within the polymerized product as it forms from the monomer composition. Because the polypropylene glycol has no polymerizable group, this material can be removed after formation of the polymerized product. Pores (i.e., void volume or free volume) are created when the previously entrained polypropylene glycol is removed. The polymeric particles resulting from the removal of the entrained polypropylene glycol are porous. In at least some embodiments, these porous polymeric particles can have hollow centers. The presence of pores or the presence of both pores and hollow centers make the polymeric particles well suited for binding or capturing target materials from a sample.

Any suitable molecular weight of poly(propylene glycol) can be used as the porogen. The molecular weight can affect the size of the pores that are formed in the polymeric particles. That is, the pore size tends to increase with the molecular weight of the poly(propylene glycol). The weight average molecular weight is often at least 500 grams/mole, at least 800 grams/mole, or at least 1000 grams/mole. The weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 grams/mole or 5000 grams/mole tends to be a liquid at room temperature. Poly(propylene glycol) that is not a liquid at room temperature can be used if it is initially dissolved in a suitable organic solvent such as an alcohol (for example, ethanol, n-propanol, or iso-propanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

In many embodiments of the first aspect, the reaction mixture used to form the porous polymeric particles includes (a) a first phase and (b) a second phase dispersed in the first phase, wherein a volume of the first phase is greater than a volume of the second phase. The first phase contains (i) a compound of Formula (II)

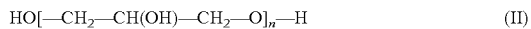

HO[—CH$_2$—CH(OH)—CH$_2$—O]$_n$—H    (II)

where the variable n is an integer equal to at least 1 and (ii) a nonionic surfactant. The second phase contains (i) a monomer composition comprising the monomer of Formula (I) as described above and (ii) a poly(propylene glycol) having a weight average molecular weight of at least 500 grams/mole. The second phase of the reaction mixture is dispersed in the first phase of the reaction mixture and the volume of the first phase is greater than the volume of the second phase. That is, the first phase can be considered to be the continuous phase and the second phase can be considered to be the dispersed phase within the continuous phase. The first phase provides a non-polymerizable medium for suspending the second phase as droplets within the reaction mixture. The second phase droplets include i) a monomer composition that can undergo polymerization and ii) a porogen, which is poly(propylene glycol) having a weight average molecular weight of at least 500 grams/mole. The monomer of Formula (I) in the second phase is typically not miscible with the first phase.

The first phase of the reaction mixture includes (i) the compound of Formula (II) and (ii) a nonionic surfactant. The first phase is typically formulated to provide a suitable viscosity and volume for dispersion of the second phase as droplets within the first phase. If the viscosity of the first phase is too high, it can be difficult to provide the requisite shear to disperse the second phase. If the viscosity is too low, however, it can be difficult to suspend the second phase and/or to form polymeric particles that are relatively uniform and well separated from each other.

Suitable compounds of Formula (II) typically have a value of n that is in a range of 1 to 20, in a range of 1 to 16, in a range of 1 to 12, in a range of 1 to 10, in a range of 1 to 6, or in a range of 1 to 4. In many embodiments, the compound of Formula (II) is glycerol where the variable n is equal to 1. Other example compounds of Formula (II) are diglycerol (n is equal to 2), polyglycerol-3 (n is equal to 3), polyglycerol-4 (n is equal to 4), or polyglycerol-6 (n is equal to 6). The polyglycerols, which can be referred to as polyglycerins, are often a mixture of materials with varying molecular weight (i.e., materials with different values for n). Polyglycerols, diglycerol, and glycerol are commercially available, for example, from Solvay Chemical (Brussels, Belgium) and Wilshire Technologies (Princeton, N.J., USA).

In addition to the compound of Formula (II), the first phase includes a nonionic surfactant. The nonionic surfactant increases the porosity on the surface of the final polymeric particles. The first phase is typically free or substantially free of an ionic surfactant that could interfere with the polymerization reaction of the monomers within the second phase. As used herein with reference to the ionic surfactant, the term "substantially free" means that no ionic surfactant is purposefully added to the first phase but may be present as a trace impurity in one of the other components in the first phase. Any impurity is typically present in an amount no greater than 0.5 weight percent, no greater than 0.1 weight percent, or no greater than 0.05 weight percent, or no greater than 0.01 weight percent based on a total weight of the first phase.

Any suitable nonionic surfactant can be used in the first phase. The nonionic surfactant often has hydroxyl group or ether linkages (for example, —CH$_2$—O—CH$_2$—) in one portion of the molecule that can hydrogen bond with other components of the reaction mixture. Suitable nonionic surfactants include, but are not limited to, alkyl glucosides, alkyl glucamides, alkyl polyglucosides, polyethylene glycol alkyl ethers, block copolymers of polyethylene glycol and polypropylene glycol, and polysorbates. Examples of suitable alkyl glucosides include, but are not limited to, octyl glucoside (also referred to as octyl-beta-D-glucopyranoside) and decyl glucoside (also referred to as decyl-beta-D-glucopyranoside). Examples of suitable alkyl glucamides include, but are not limited to, octanoyl-N-methylglucamide, nonanoyl-N-methylglucamide, and decanoyl-N-methylglucamide. These surfactants can be obtained, for example, from Sigma Aldrich (St. Louis, Mo., USA) or Spectrum Chemicals (New Brunswick, N.J., USA). Examples of suitable alkyl polyglucosides include, but are not limited to, those commercially available from Cognis Corporation (Monheim, Germany) under the trade designation APG (for example, APG 325) and those commercially available from Dow Chemical (Midland, Mich., USA) under the trade designation TRITON (for example, TRITON BG-10 and TRITON CG-110). Examples of polyethylene glycol alkyl ethers include, but are not limited to, those commercially available under the trade designation BRIJ (for example, BRIJ 58 and BRIJ 98) from Sigma Aldrich (St. Louis, Mo., USA). Examples of block copolymers of polyethylene glycol and polypropylene glycol include, but are not limited to, those commercially available under the trade designation PLURONIC from BASF (Florham Park, N.J., USA). Examples of polysorbates include, but are not limited to, those commercially available under the trade designation TWEEN from ICI American, Inc. (Wilmington, Del., USA).

The surfactant can be present in the first phase in any suitable amount. Often, the surfactant is present in an amount equal to at least 0.5 weight percent, at least 1 weight percent, or at least 2 weight percent based on a total weight of the first phase. The surfactant can be present in an amount up to 15 weight percent, up to 12 weight percent, or up to 10 weight percent based on a total weight of the first phase. For example, the surfactant is often present in the first phase in an amount in a range of 0.5 to 15 weight percent, in a range of 1 to 12 weight percent, in a range of 0.5 to 10 weight percent, or in a range of 1 to 10 weight percent based on the total weight of the first phase.

Optionally, water or an organic solvent that is miscible with the compound of Formula (II) can be present in the first reaction mixture. Suitable organic solvents include, for example, an alcohol such as methanol, ethanol, n-propanol, or isopropanol. The amount of any optional water or organic solvent is selected so that the desired viscosity of the first phase can be achieved. The amounts of the optional water or organic solvent is often no greater than 10 weight percent, no greater than 5 weight percent, or no greater than 1 weight percent based on the total weight of the first phase. If higher amounts of water are included, the porosity may decrease. In some embodiments, the first phase is free or substantially free of the optional water or organic solvent. As used herein with reference to the optional water or organic solvent, the term "substantially free" means that water or organic solvent is not purposely added to the first phase but may be present as an impurity in one of the other components in the first phase. For example, the amount of the optional water or organic solvent is less than 1 percent, less than 0.5 weight percent, or less than 0.1 weight percent based on a total weight of the first phase.

The reaction mixture includes a second phase dispersed in the first phase. The second phase includes both i) a monomer composition and ii) a poly(propylene glycol) having a weight average molecular weight of at least 500 grams/mole. The monomer composition is polymerized in the second phase to from the polymeric particles. The polypropylene glycol functions as a porogen that gets partially entrained within the polymerized product as it is formed from the monomer composition.

The volume of the first phase is greater than the volume of the second phase. The volume of the first phase is sufficiently large compared to the volume of the second phase so that the second phase can be dispersed in the form of droplets within the first phase. Within each droplet, the monomer composition is polymerized to form a polymerized product. To form particles from the second phase, the volume ratio of the first phase to the second phase is typically at least 2:1. As the volume ratio increases (for example, when the ratio is at least 3:1, at least 4:1, or at least 5:1), beads can be formed that have a relatively uniform size and shape. If the volume ratio is too large, however, the reaction efficiency is diminished (i.e., a smaller amount of polymeric particles is produced). The volume ratio is generally no greater than 25:1, no greater than 20:1, no greater than 15:1, or no greater than 10:1.

In some embodiments, the first monomer of Formula (I) as described above is the only monomer in the monomer composition of the second phase. In other embodiments, the first monomer of Formula (I) can be used in combination with at least one second monomer. The second monomer has a single free radically polymerizable group such as an ethylenically unsaturated group, which is often a (meth)acryloyl group of formula $H_2C=CR^1—(CO)—$ where $R^1$ is hydrogen or methyl. Suitable second monomers are not miscible with the first phase but can be miscible or not miscible with the first monomer of Formula (I). The second monomer is often added to alter the hydrophobicity or hydrophilicity of the porous polymeric material. The addition of these monomers can, however, diminish the porosity of the polymeric particles and/or increase the size of the polymeric particles.

Some example second monomers are of Formula (III).

$$CH_2=CR^1—(CO)—O—Y—R^2 \qquad (III)$$

In this formula, group $R^1$ is hydrogen or methyl. In many embodiments, $R^1$ is hydrogen. Group Y is a single bond, alkylene, oxyalkylene, or poly(oxyalkylene). Group $R^2$ is a carbocyclic group or heterocyclic group. These second monomers tend to be miscible with the first monomer of Formula (I) in the second phase but are not miscible with the first phase.

As used herein, the term "alkylene" refers to a divalent group that is a radical of an alkane and includes groups that are linear, branched, cyclic, bicylic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene groups. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. The oxyalkylene is often oxyethylene or oxypropylene. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms. The poly(oxyalkylene) is often poly(oxyethylene), which can be referred to as poly(ethylene oxide) or poly(ethylene glycol).

Carbocyclic $R^2$ groups can have a single ring or can have multiple rings such as fused rings or bicyclic rings. Each ring can be saturated, partially unsaturated, or unsaturated. Each ring carbon atom can be unsubstituted or substituted with alkyl groups. Carbocyclic groups often has 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like. Any of these carbocyclic groups can be substituted with an alkyl group having 1 to 20 carbon atoms, 1 to 10 carbon atoms, 1 to 6 carbon atoms, or 1 to 4 carbon atoms.

Heterocyclic $R^2$ groups can have a single ring or multiple rings such as fused rings or bicyic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (III) for use as the second monomer include, but are not limited to, benzyl (meth)acrylate, 2-phenoxyethyl (meth)acrylate (commercially available from Sartomer under the trade designation SR339 and SR340), isobornyl (meth)acrylate, tetrahydrofurfuryl (meth)acrylate (commercially available from Sartomer under the trade designation SR285 and SR203), 3,3,5-trimethylcyclohexyl (meth)acrylate (commercially available from Sartomer under the trade designation CD421 and CD421A), and ethoxylated nonyl phenol acrylate (commercially available from Sartomer under then trade designation SR504, CD613, and CD612).

Other example second monomers are alkyl (meth)acrylates of Formula (IV).

$$CH_2=CR^1—(CO)—O—R^3 \qquad (IV)$$

In Formula (IV), group $R^1$ is hydrogen or methyl. In many embodiments, $R^1$ is hydrogen. Group $R^3$ is a linear or branched alkyl having 1 to 20 carbon atoms, 1 to 10 carbon atoms, 1 to 6 carbon atoms, or 1 to 4 carbon atoms. These second monomers tend to be miscible with the first monomer of Formula (I) in the second phase but are not miscible with the first phase.

Examples of alkyl (meth)acrylates of Formula (IV) include, but are not limited to, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, 2-methylbutyl (meth)acrylate, n-hexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth)acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth)acrylate, and heptadecanyl (meth)acrylate.

In some embodiments, the only monomers in the monomer composition are the first monomer of Formula (I) and the second monomer of Formula (III), Formula (IV), or both. Any suitable amounts of the first monomer and second monomer can be used provided that the monomer composition contains at least 10 weight percent of the first monomer of Formula (I). The addition of a second monomer of Formula (III), Formula (IV), or both tends to increase the hydrophobicity of the porous polymeric particles. The monomer composition often contains 10 to 90 weight percent of the first monomer and 10 to 90 weight percent of the second monomer based on a total weight of monomers in the monomer composition. For example, the second phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of monomers in the monomer composition.

Depending on the final use of the polymeric particles prepared, it can be desirable to include at least one hydrophilic second monomer in the monomer composition. The addition of a hydrophilic second monomer tends to make the polymeric particles more suitable for applications where the particles will be exposed to aqueous-based materials such as aqueous-based samples. Additionally, the use of a hydrophilic second monomer allows the porous polymeric particles to be dispersed in water more easily during the preparation of the porous article using, for example, a wetlaid process. Hydrophilic second monomers are selected so that they are not miscible with the first phase. These monomers may or may not be miscible with the first monomer of Formula (I).

Some example hydrophilic second monomers are hydroxyl-containing monomers of Formula (V).

$$CH_2=CR^1-(CO)-O-R^4 \quad (V)$$

In Formula (V), group $R^1$ is hydrogen or methyl. In many embodiments, $R^1$ is hydrogen. Group $R^4$ is an alkyl substituted with one or more hydroxyl groups or a group of formula $-(CH_2CH_2O)_qCH_2CH_2OH$ where q is an integer equal to at least 1. The alkyl group typically has 1 to 10 carbon atoms, 1 to 6 carbon atoms, 1 to 4 carbon atoms, or 1 to 3 carbon atoms. The number of hydroxyl groups is often in a range of 1 to 3. The variable q is often in a range of 1 to 20, in a range of 1 to 15, in a range of 1 to 10, or in a range of 1 to 5. In many embodiments, the second monomer of Formula (IV) has a single hydroxyl group.

Example monomers of Formula (V) include, but are not limited to, 2-hydroxyethyl (meth)acrylate, 2-hydroxypropyl (meth)acrylate, 3-hydroxypropyl (meth)acrylate, and 4-hydroxybutyl (meth)acrylate), 2-hydroxylbutyl (meth)acrylate, polyethylene glycol mono(meth)acrylate (for example, monomers commercially available from Sartomer (Exton, Pa., USA) under the trade designation CD570, CD571, and CD572), and glycol mono(meth)acrylate.

Other example hydrophilic second monomers are hydroxyl-containing monomers of Formula (VI).

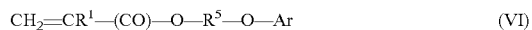

$$CH_2=CR^1-(CO)-O-R^5-O-Ar \quad (VI)$$

In Formula (VI), group $R^1$ is hydrogen or methyl. In many embodiments, $R^1$ is hydrogen. Groups $R^5$ is an alkylene substituted with at least one hydroxyl group. Suitable alkylene groups often have 1 to 10 carbon atoms, 1 to 6 carbon atoms or 1 to 4 carbon atoms. The alkylene group $R^5$ can be substituted with 1 to 3 hydroxyl groups but is often substituted with a single hydroxyl group. The group Ar is an aryl group having 6 to 10 carbon atoms. In many embodiments, the Ar group is phenyl. One example monomer of Formula (VI) is 2-hydroxy-2-phenoxypropyl (meth)acrylate.

If the second monomer is of Formula (V) or (VI), which are hydroxyl-containing monomers, the amount of this monomer that can be combined with the first monomer of Formula (I) is often no greater than 2 weight percent based on a total weight of monomers in the monomer composition. If greater than about 2 weight percent of the second monomer of Formula (V) or (VI) is used, the resulting polymeric particles tend to have diminished porosity.

Other hydrophilic monomers can be used as the second monomers in larger quantities than the second monomers of Formula (V) or (VI) without diminishing the porosity of the resulting polymeric particles. For example, sulfonic acid-containing monomers of Formula (VII) can be included in the monomer composition along with the first monomer of Formula (II) or a salt thereof.

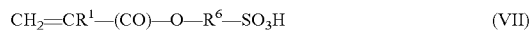

$$CH_2=CR^1-(CO)-O-R^6-SO_3H \quad (VII)$$

In Formula (VII), group $R^1$ is hydrogen or methyl. In many embodiments, $R^1$ is hydrogen. Group $R^6$ is an alkylene having 1 to 10 carbon atoms, 1 to 6 carbon atoms, or 1 to 4 carbon atoms. Examples of sulfonic acid-containing monomers of Formula (VII) include, but are not limited to, sulfoethyl (meth)acrylate and sulfopropyl (meth)acrylate. Depending on the pH conditions, these second monomers can impart an ionic (for example, anionic) character to the porous polymeric particles. The counter ion is often a cation of such as an alkali metal ion, an alkaline earth metal ion, an ammonium ion, or an alkyl substituted ammonium ions such as tetraalkyl ammonium ion.

If the second monomer is a sulfonic acid-containing monomer of Formula (VII), the monomer composition can contain up to 20 weight percent of this monomer based on a total weight of monomers in the monomer composition. In some embodiments, the only monomers in the monomer composition are the first monomer of Formula (I) and the second monomer of Formula (VII). The monomer composition often contains 80 to 99 weight percent of the first monomer of Formula (I) and 1 to 20 weight percent of the second monomer of Formula (VII) based on a total weight of monomers in the monomer composition. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

In other embodiments, the monomer composition includes a first monomer of Formula (I) and two second monomers. The two second monomers are a sulfonic acid-containing monomer, such as those of Formula (VII), and a hydroxyl-containing monomer, such as those of Formula (V) or (VI). When the hydroxyl-containing monomer is combined with a sulfonic acid-containing monomer, higher amounts of the hydroxyl-containing monomer can be added to the monomer composition without substantially decreasing the porosity of the resulting polymeric particles. That is, the amount of the hydroxyl-containing monomer can be greater than 2 weight percent based on the weight of the monomers in the monomer composition. The monomer composition often contains 80 to 99 weight percent of the first monomer of Formula (II) and 1 to 20 weight percent of the second monomer, wherein the second monomer is a mixture of the sulfonic acid-containing monomer and the hydroxyl-containing monomer. Up to 50 weight percent, up to 40 weight percent, up to 20 weight percent, or up to 10 weight percent of the second monomer can be the hydroxyl-containing monomer.

Other second monomers that can impart an ionic (for example, anionic) character to the porous polymeric particles have a carboxylic acid group (—COOH). Examples of such monomers include, but are not limited to, (meth)acrylic acid, maleic acid, and β-carboxyethyl acrylate. If a monomer having a carboxylic acid group is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (I) and 1 to 20 weight percent of the second monomer having a carboxylic acid group. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Still other hydrophilic monomers are those of Formula (VIII)

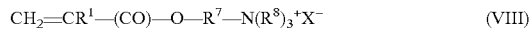

$$CH_2=CR^1—(CO)—O—R^7—N(R^8)_3{}^+X^- \qquad (VIII)$$

having a quaternary ammonium group. The group $R^7$ is an alkylene having 1 to 10 carbon atoms, 1 to 6 carbon atoms, or 1 to 4 carbon atoms. The group $R^8$ is an alkyl having 1 to 4 carbon atoms or 1 to 3 carbon atoms. The anion $X^-$ can be any anion but is often a halide such as chloride. Alternatively the anion can be a sulfate and be associated with two ammonium-containing cationic monomers. Examples include, but are not limited to, (meth)acrylamidoalkyltrimethylammonium salts (for example, 3-methacrylamidopropyltrimethylammonium chloride and 3-acrylamidopropyltrimethylammonium chloride) and (meth)acryloxyalkyltrimethylammonium salts (for example, 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate). Depending on the pH conditions, these third monomers can impart an ionic (for example, cationic) character to the porous polymeric particles.

If a second monomer of Formula (VIII) is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (I) and 1 to 20 weight percent of the second monomer of Formula (VIII). For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Often if an ionic monomer is added such as one having a carboxylic acid group or a salt thereof, a sulfonic acid group or a salt thereof (such as of Formula (VII)), or an ammonia group (such as of Formula (VIII)), the ionic monomer is often present in low amounts such as in a range of 1 to 10 weight percent, in a range of 1 to 5 weight percent, or in a range of 1 to 3 percent based on the total weight of monomers in the monomer composition. Particularly when the preparation of porous polymeric particles having an average diameter less than about 10 micrometers, less than about 5 micrometers, less than about 4 micrometers, or less than about 3 micrometers are desired, lower concentrations of the ionic monomers in the monomer composition may be preferred. For capture of hydrophobic materials or nonionic materials, it may be preferable to have monomer compositions that are free or substantially free of ionic monomers. As used herein in reference to the amount of ionic monomers, "substantially free" means that no such monomer is intentionally added or is added at an amount no greater than 1 weight percent, no greater than 0.5 weight percent, no greater than 0.2 weight percent, or no greater than 0.1 weight percent based on the total weight of monomers in the monomer composition.

In some embodiments, it is preferable that the monomer composition contains only a monomer of Formula (I) or a mixture of a first monomer of Formula (I) and a second monomer of Formula (III) added to increase the hydrophobicity of the porous polymeric particles. For example, some monomer compositions often contains 10 to 90 weight percent of the first monomer and 10 to 90 weight percent of the second monomer based on a total weight of monomers in the monomer composition. For example, the monomer composition can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer.

The monomer composition can optionally contain a third monomer with at least two polymerizable groups. The polymerizable groups are typically (meth)acryloyl groups. In many embodiments, the third monomer has two or three (meth)acryloyl groups. The third monomer typically is not miscible with the first phase and may or may not be miscible with the first monomer of Formula (I).

Some third monomers have a hydroxyl group. Such monomers can function as crosslinkers like the first monomer of Formula (I) but can provide polymeric particles with increased hydrophilic character. An example hydroxyl-containing third monomer is glycerol di(meth)acrylate.

Some third monomers are selected to have at least three polymerizable groups. Such third monomers can be added to provide more rigidity to the resulting polymeric particles. The addition of these third monomers tends to minimize swelling of the polymeric particles when exposed to water. Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris (2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer composition, any suitable amount can be used. The third monomer is often used in an amount up to 20 weight percent based on the total weight of monomers in the monomer composition. In some embodiments, the amount of the third monomer is up to 15 weight percent, up to 10 weight percent, or up to 5 weight percent.

In some embodiments, the monomer composition contains at least 10 weight percent, at least 20 weight percent, at least 30 weight percent, at least 35 weight percent, at least 40 weight percent, at last 45 weight percent, at least 50 weight percent, at least 55 weight percent, at least 60 weight percent, at least 65 weight percent, at least 70 weight percent, at least 75 weight percent at least 80 weight percent, at least 90 weight percent, or at least 95 weight percent of the first monomer of Formula (I). The remaining amount of the monomer composition can include any combination of the second and third monomers described above. In some embodiments, any remaining amount is a monomer of Formula (III).

The monomer composition often contains 10 to 100 weight percent of the first monomer, 0 to 90 weight percent of the second monomer, and 0 to 20 weight percent of the third monomer based on a total weight of monomers in the monomer composition. For example, the monomer composition can contain 10 to 90 weight percent of the first monomer, 10 to 90 weight percent of the second monomer, and 0 to 20 weight percent of the third monomer. The monomer composition can contain 10 to 89 weight percent of the first monomer, 10 to 89 weight percent of the second monomer, and 1 to 20 weight percent of the third monomer based on a total weight of the monomer composition.

In addition to the monomer composition, the second phase contains poly(propylene glycol), which functions as a porogen. The poly(propylene glycol) is soluble in the monomer composition within the second phase but is dispersible within the first phase. Stated differently, the poly(propylene glycol) is completely miscible with the second phase and partially miscible with the first phase. The poly(propylene glycol) is removed after polymerization of the monomer composition to provide pores (for example, void volumes or free volumes) in the polymeric particle. The poly(propylene glycol) does not have any polymerizable groups (i.e., it is not a monomer) and, in general, is not covalently attached to the polymeric particles that forms within the second phase. It is believed that some of the poly(propylene glycol) become entrained within the polymerized product. It is further believed that some of the poly(propylene glycol) is positioned on the interface between the first phase and the second phase as the polymerized product is formed in the second phase. The presence of the poly(propylene glycol) at the surface of the forming polymerized product results in the formation of a polymeric particle having surface porosity. The surface porosity can be seen from electron micrographs of the polymeric particles such as in FIG. 1.

The second phase can contain up to 50 weight percent poly(propylene glycol). If higher amounts of the poly(propylene glycol) are used, there may be an insufficient amount of the monomer composition included in the second phase to form polymeric particles that are uniformly shaped. In many embodiments, the second phase can contain up to 45 weight percent, up to 40 weight percent, up to 35 weight percent, up to 30 weight percent, or up to 25 weight percent poly(propylene glycol) based on a total weight of the second phase. The second phase typically contains at least 5 weight percent poly(propylene glycol). If lower amounts of the poly(propylene glycol) are used, the porosity of the resulting polymeric particles may be insufficient. The second phase typically can contain at least 10 weight percent, at least 15 weight percent, or at least 20 weight percent poly(propylene glycol). In some embodiments, the second phase contains 5 to 50 weight percent, 10 to 50 weight percent, 10 to 40 weight percent, 10 to 30 weight percent, 20 to 50 weight percent, 20 to 40 weight percent, or 25 to 35 weight percent poly(propylene glycol) based on the total weight of the second phase.

In some embodiments, the second phase contains 50 to 90 weight percent monomer composition and 10 to 50 weight percent poly(propylene glycol), 60 to 90 weight percent monomer composition and 10 to 40 weight percent poly(propylene glycol), 50 to 80 weight percent monomer composition and 20 to 50 weight percent poly(propylene glycol), or 60 to 80 weight percent monomer composition and 20 to 40 weight percent poly(propylene glycol) based on a total weight of the second phase.

In addition to the monomer composition and poly(propylene glycol), the second phase often contains an initiator for free radical polymerization of the monomer composition. Any suitable initiator known in the art can be used. The initiator can be a thermal initiator, a photoinitiator, or both. The specific initiator used is often selected based on its solubility in the second phase. The initiator is often used at a concentration of 0.1 to 5 weight percent, 0.1 to 3 weight percent, 0.1 to 2 weight percent, or 0.1 to 1 weight percent based on the weight of monomers in the monomer composition.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides and azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (for example, benzoin methyl ether and substituted benzoin alkyl ethers such anisoin methyl ether), phenones (for example, substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (for example, commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (for example, commercially available under the trade designation DAROCUR 4265 from Ciba Specialty Chemicals), 2,2-dimethoxy-1,2-diphenylethan-1-one (for example, commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (for example, commercially available under the trade designation IRGACURE 1800 from Ciba Specialty Chemicals), a mixture of bis(2,6-dimethoxybenzoyl)-2,4,4-trimethyl-pentylphosphine oxide (for example, commercially available under the trade designation IRGACURE 1700 from Ciba Specialty Chemicals), 2-methyl-1[4-(methylthio)phenyl]-2-morpholinopropan-1-one (for example, commercially available under the trade designation IRGACURE 907 from Ciba Specialty Chemicals), 1-hydroxy-cyclohexyl-phenyl-ketone (for example, commercially available under the trade designation IRGACURE 184 from Ciba Specialty Chemicals), 2-benzyl-2-(dimethylamino)-1-[4-(4-morpholinyl)phenyl]-1-butanone (for example, commercially available under the trade designation IRGACURE 369 from Ciba Specialty Chemicals), bis(2,4,6-trimethylbenzoyl)-phenylphosphine oxide (for example, commercially available under the trade designation IRGACURE 819 from Ciba Specialty Chemicals), ethyl 2,4,6-trimethylbenzoyldiphenyl phosphinate (for example, commercially available from BASF, Charlotte, N.C. under the trade designation LUCIRIN TPO-L), and 2,4,6-trimethylbenzoyldiphenylphosphine oxide (for example, commercially available from BASF, Charlotte, N.C. under the trade designation LUCIRIN TPO).

The reaction mixture often includes at least 5 weight percent of the second phase (dispersed phase) and up to 95 weight percent of the first phase (continuous phase). In some embodiments, the reaction mixture contains 5 to 40 weight percent second phase and 60 to 95 weight percent first phase, 5 to 30 weight percent second phase and 70 to 95 weight percent first phase, 10 to 30 weight percent second phase and 70 to 90 weight percent first phase, or 5 to 20 weight percent second phase and 80 to 95 weight percent first phase. The weight percents are based on a total weight of the reaction mixture.

To prepare the polymeric particles or beads, droplets of the second phase are formed in the first phase. The components of the second phase are often mixed together prior to addition to the first phase. For example, the monomer composition, initiator, and the poly(propylene glycol) can be blended together and then this blended composition, which is the second phase, can be added to the first phase. The resulting reaction mixture is often mixed under high shear to form a micro-emulsion. The size of the dispersed second phase droplets can be controlled by the amount of shear or the mixing rate. The size of the droplets can be determined by placing a sample of the mixture under an optical microscope prior to polymerization. Although any desired droplet size can be used, the average droplet diameter is often less than 200 micrometers, less than 100 micrometers, less than 50 micrometers, less than 25 micrometers, less than 10 micrometers, or less than 5 micrometers. For example, the average droplet diameter can be in the range of 1 to 200 micrometers, 1 to 100 micrometers, 5 to 100 micrometers, 5 to 50 micrometers, 5 to 25 micrometers, or 5 to 10 micrometers.

If a photoinitiator is used, the reaction mixture is often spread on a non-reactive surface at a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer composition and form polymeric particles.

The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the first phase and the dispersed second phase.

During the polymerization reaction, the monomer composition reacts within the second phase droplets suspended in the first phase. As polymerization progresses, the poly(propylene glycol) included in the second phase gets partially entrained within the polymerized product. Although it is possible that some portion of the poly(propylene glycol) can be covalently attached to the polymeric product through a chain transfer reaction, preferably the poly(propylene glycol) is not bonded to the polymeric product. The polymerized product is in the form of particles. In some embodiments, the particles are polymeric beads having a relatively uniform size and shape.

After formation of the polymerized product (i.e., polymeric particles containing entrained poly(propylene glycol)), the polymerized product can be separated from the first phase. Any suitable separation method can be used. For example, water is often added to lower the viscosity of the first phase. Particles of the polymerized product can be separated from the other components by decantation, filtration, or centrifugation. The particles of the polymerized product can be further washed by suspending them in water and collecting them a second time by decantation, filtration, or centrifugation.

The particles of the polymerized product can then be subjected to one or more washing steps to remove the poly(propylene glycol) porogen. Suitable solvents for removing the poly(propylene glycol) include, for example, acetone, methyl ethyl ketone, toluene, and alcohols such as ethanol, n-propanol, or iso-propanol. Stated differently, the entrained poly(propylene glycol) is removed from the polymerized product using solvent extraction methods. Pores are created where the poly(propylene glycol) previously resided.

In many embodiments, the resulting porous polymeric particles (the polymerized product after removal of the poly(propylene glycol) porogen) have an average diameter that is less than 200 micrometers, less than 100 micrometers, less than 50 micrometers, less than 25 micrometers, less than 10 micrometers, or less than 5 micrometers. For example, the porous polymeric particles can have an average diameter in the range of 1 to 200 micrometers, 1 to 100 micrometers, 1 to 50 micrometers, 1 to 25 micrometers, 1 to 10 micrometers, or 1 to 5 micrometers. The particles are often in the form of beads.

The polymeric particles usually have multiple pores distributed over the surface of the particles. In some embodiments, the polymeric particles are hollow in addition to having multiple pores distributed over the surface of the particles. After removal of the poly(propylene glycol) porogen, the resulting polymeric particles tend to be more porous than polymeric particles prepared using a first phase that is predominately water.

The porous article includes the porous polymeric particles distributed in a fibrous porous matrix. The fibrous porous matrix can be either woven or non-woven. In many embodiments, the porous article includes porous polymeric particle enmeshed within a nonwoven, fibrous porous matrix. The nonwoven, fibrous porous matrix is often in the form of a layer of interlaid fibers that are not woven or knitted together. The nonwoven, fibrous porous matrix can be prepared by any suitable process such as, for example, air laying techniques, spunlaid techniques such as meltblowing or spunbonding, carding, wetlaying, and combinations thereof. In some applications, it may be preferable to prepare the fibrous nonwoven matrix by spunlaid or wetlaid techniques.

Fibers suitable for use in preparing the nonwoven, fibrous porous matrix are usually pulpable or extrudable fibers such as those that are stable to radiation and/or to a variety of solvents. Useful fibers include polymeric fibers, inorganic fibers, and combinations thereof. In many embodiments, the fibers include polymeric fibers and often include a plurality of different types of polymeric fibers. For example, at least some of the polymeric fibers can be selected to exhibit a degree of hydrophilicity.

Suitable polymeric fibers include those made from natural polymers (those derived from animal or vegetable sources) and/or synthetic polymers, including thermoplastic and solvent-dispersible polymers. Useful polymers include wool; silk; cellulosic polymers (for example, cellulose, cellulose derivatives such as rayon, and the like); fluorinated polymers (for example, poly(vinyl fluoride), poly(vinylidene fluoride), copolymers of vinylidene fluoride such as poly (vinylidene fluoride-co-hexafluoropropylene), copolymers of chlorotrifluoroethylene such as poly(ethylene-co-chlorotrifluoroethylene), and the like); chlorinated polymers; polyolefins (for example, polyethylene, polypropylene, poly(l-butene), copolymers of ethylene and propylene, alpha olefin copolymers such as copolymers of ethylene or propylene with 1-butene, 1-hexene, 1-octene, and 1-decene such as poly(ethylene-co-1-butene), poly(ethylene-co-1-butene-co-1-hexene), and the like); poly(isoprenes); poly(butadienes); polyamides (for example, nylon 6, nylon 6,6, nylon 6,12, poly(iminoadipoyliminohexamethylene), poly(iminoadipoyliminodecamethylene), polycaprolactam, and the like); polyimides (for example, poly(pyromellitimide) and the like); polyethers; poly(ether sulfones) (for example, poly (diphenylether sulfone), poly(diphenylsulfone-co-diphenylene oxide sulfone), and the like); poly(sulfones); poly (vinyl esters) such as poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl ethers); poly(vinyl alcohols); polyaramids (for example, para-aramids such as poly (paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly(carbonates); and the like; and combinations thereof.

In some embodiments, mixtures of hydrophobic and hydrophilic polymeric fibers are used. For example, the fibrous porous matrix can include a mixture of hydrophilic fibers such as polyamides and polysulfones plus hydrophobic fibers such as polyolefins. In some specific examples, the polymeric fibers include polyamides, polyolefins, polysulfones, and combinations thereof. An even more specific example includes nylon, polyethylene, polypropylene, and combinations thereof.

Suitable inorganic fibers include those that contain at least one inorganic material selected from glasses, ceramics, and combinations thereof. These fibers are often added to provide strength to the fibrous porous matrix. For example, porous matrix layers containing inorganic fibers are often capable of being bent, folded, or pleated without breaking apart. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass and combinations thereof.

The fibers used to form the nonwoven fibrous porous matrix can be of a length and diameter that can provide a porous matrix having sufficient structural integrity and sufficient porosity for a particular application (for example, for a particular type of sample). The fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, at least 20 millimeters, at least 25 millimeters, or at least 30 millimeters. The diameter of the fibers can be, for example, at least 10 micrometers, at least 20 micrometers, at least 40 micrometers, or at least 60 micrometers. The fiber lengths and diameters will vary depending upon factors such as the nature of the fiber and the type of application.

To facilitate entrapment of the porous polymeric particles and/or to ensure a high surface area, the fibers used to form the nonwoven, fibrous porous matrix often contain at least one fibrillated fiber (for example, in the form of a main fiber surrounded by many smaller attached fibrils). The main fiber generally can have a length in the range of 0.5 millimeters to 5 millimeters and a diameter in a range of 1 micrometer to 20 micrometers. The fibrils typically can have a sub-micrometer diameter. In many embodiments, the fibrillated fibers are prepared from a polyolefin such as polyethylene or polypropylene.

The nonwoven, fibrous porous matrix can contain a plurality of different types of fibers. In some embodiments, the porous matrix can be formed using two, three, four, or even more different types of fibers. For example, a nylon fiber can be added for strength and integrity, while fibrillated polyethylene can be added for entrapment of the particulates. Additionally, the nylon fiber provides hydrophilic character while the fibrillated polyethylene provides hydrophobic character to the porous matrix. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1.

The nonwoven, fibrous porous matrix often further contains at least one polymeric binder. Suitable polymeric binders include natural and synthetic polymeric materials that are relatively inert (exhibiting little or no chemical interaction with either the fibers or the porous polymeric particles). Useful polymeric binders include polymeric resins (for example, in the form of powders and latexes), polymeric binder fibers, and the like, and combinations thereof.

Suitable polymeric resins for used in the nonwoven, fibrous porous matrix include, but are not limited to, natural rubbers, neoprene, styrene-butadiene copolymers, acrylate resins, polyvinyl chloride, polyvinyl acetate, and combinations thereof. In many embodiments, the polymeric resin includes acrylate resins.

Suitable polymeric binder fibers include adhesive-only type fibers and bi-component fibers. Example adhesive-only type fibers include those commercially available under the trade designation KODEL (for example, KODEL 43UD) from Eastman Chemical Products (Kingsport, Tenn., USA). Bi-component fibers can be, for example, side-by-side forms, sheath-core forms, or the like. An example side-by-side bi-component fiber is the polyolefin thermally bonded bi-component fiber that is commercially available from Chisso Corporation (Osaka, Japan) under the trade designation CHISSO (for example, CHISSO ES). An example sheath-core bi-component fiber is commercially available from Unitika Ltd. (Osaka, Japan) under the trade designation MELTY (for example, MELTY 4080) and those commercially available from Minifibers, Inc. (Johnson City, Tenn.) made of ethyl vinyl acetate (sheath) and polypropylene (core). The binder is the sheath portion of the sheath-core bi-component fiber.

The nonwoven, fibrous porous matrix often includes a mixture of polyolefin fibers, polyamide fibers, glass fibers, and polymeric binder. In some particular embodiments, the nonwoven, fibrous porous matrix contains a mixture of nylon fibers, fibrillated polyethylene fibers, glass fibers, and polymeric binder fibers (e.g. sheath-core bi-component fiber). In some examples, the nonwoven, fibrous porous matrix contains 40 to 80 weight percent fibrillated polyethylene fibers, 10 to 30 weight percent nylon fibers, 5 to 20 weight percent glass fibers, and 5 to 20 weight percent polymer binder fibers. In other examples, the nonwoven, fibrous porous matrix contains 50 to 70 weight percent fibrillated polyethylene fibers, 10 to 25 weight percent nylon fibers, 5 to 15 weight percent glass fibers, and 5 to 20 weight percent polymeric binder fibers. In still other examples, the fibrous porous matrix contains 55 to 65 weight percent fibrillated polyethylene fibers, 10 to 20 weight percent nylon fibers, 5 to 15 weight percent glass fibers, and 10 to 20 weight percent polymeric binder fibers.

In many embodiments, the fibrous porous matrix contains only fibers and binder. For example, at least 90 weight percent, at least 95 weight percent, at least 98 weight percent, at least 99 weight percent, or at least 99.5 weight percent of a dry fibrous porous matrix is either fibers or binder.

The porous article includes both the fibrous porous matrix and porous polymeric particles distributed throughout the fibrous porous matrix. In most embodiments, the porous article contains at least 10 weight percent porous polymeric particles based on a total dry weight of the porous article. If the amount of the porous polymeric particles is lower than about 10 weight percent, the porous article may not contain enough porous polymeric particles to effectively separate target materials from a fluid stream. In some examples, the porous article contains at least 15 weight percent, at least 20 weight percent, at least 25 weight percent, or at least 30 weight percent porous polymeric particles based on a total dry weight of the porous article.

On the other hand, the porous article usually contains no greater than 55 weight percent porous polymeric particles based on the total dry weight of the porous article. If the amount of the porous polymeric particles is greater than about 55 weight percent, the porous article may contain an insufficient amount of the fibrous porous matrix. That is, the strength of the porous article may be insufficient to hold together when contacted with a fluid stream. In some examples, the porous article contains no greater than 50 weight percent, no greater than 45 weight percent, or no greater than 40 weight percent porous polymeric particles based on a total weight of the porous article.

Stated differently, the porous article often contains 10 to 55 weight percent porous polymeric particles and 45 to 90 weight percent fibrous porous matrix, 15 to 50 weight percent porous polymeric particles and 50 to 85 weight percent fibrous porous matrix, 20 to 50 weight percent porous polymeric particles and 50 to 80 weight percent fibrous porous matrix, 20 to 45 weight percent porous polymeric particles and 55 to 80 weight percent fibrous porous matrix, 25 to 40 weight percent porous polymeric particles and 60 to 75 weight percent fibrous porous matrix, or 30 to 40 weight percent porous polymeric particles and 60 to 70 weight percent fibrous porous matrix. The amounts are based on the total dry weight of the porous article.

In many embodiments, the porous article (when dry) contains only porous polymeric particles and fibrous porous matrix. For example, the porous article contains at least 90 weight percent, at least 95 weight percent, at least 98 weight percent, at least 99 weight percent, or at least 99.5 weight percent combined porous polymeric particles and fibrous porous matrix when dry.

Preferably, any polymeric binder included in the fibrous porous matrix does not substantially adhere to the porous polymeric particles in the porous article. In other words, when the porous article is examined by scanning electron microscopy, less than 5 percent of a total surface area of the porous polymeric particle is covered with polymeric binder. For example, less than 4 percent, less than 3 percent, less than 2 percent, or even less than 1 percent of the total surface area of the porous polymeric particle is covered with the polymeric binder.

In a second aspect, a method of making a porous article is provided. The method includes a) providing a plurality of porous polymeric particles and b) distributing the porous polymeric particles throughout a fibrous porous matrix. The porous polymeric particles are the same as those described above and can be prepared using the methods described above. Any suitable method can be used to distribute the porous polymeric particle throughout the fibrous porous matrix. In many embodiments, the porous polymeric particles are enmeshed within the fibrous porous matrix.

In one specific method, the porous article is prepared using a wet laying or "wetlaid" process. In this process, a dispersion is formed that contains (a) a plurality of fibers, (b) a plurality of porous polymeric particles, (c) an optional polymeric binder, (d) and a dispersing liquid such as water, a water-miscible organic solvent, or a mixture thereof. The fibers, porous polymeric particles, and polymeric binder components can be dispersed together in the dispersing liquid. Alternatively, one or two of these components can be dispersed prior to the introduction of the other components. In some embodiments, the fibers (for example, hydrophobic fibers) have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process often additionally includes at least partially depositing the polymeric binder onto at least a portion of the fibers and removing the dispersing liquid from the dispersion. Deposition of the polymeric binder onto the fibers can be carried out either before or after the dispersing liquid removal or dewatering step, depending upon the nature of the polymeric binder. For example, when polymeric latex is used as the polymeric binder, the polymeric latex can be precipitated onto the fibers before or after porous polymeric particles particle addition and prior to dewatering. After the initial dewatering, heat can be applied to finish the dewatering and to set the resulting deposited latex. When polymeric binder fibers are used as the polymeric binder, dewatering can generally be carried out first, followed by heating to finish the dewatering and to melt the polymeric binder fibers (and thereby deposit polymeric binder on the fibers).

One or more adjuvants or additives can be used in preparing this type of porous article. Useful adjuvants include process aids (for example, precipitation agents such as sodium aluminates and aluminum sulfate, which can aid in precipitating the polymeric binder onto the fibers), materials that can enhance the overall performance of the resulting porous article, and the like. When used, the amounts of such adjuvants can be present, for example, in an amount up 5 weight percent, up to 4 weight percent, up to 3 weight percent, up to 1 weight percent, or up to 0.5 weight percent based on a total dry weight of the porous article (for example, fibers, porous polymeric particles, and polymeric binder). The total amount of adjuvants is typically selected to be as low as possible so as to maximize the amount of porous polymeric particles that can be included in the porous article.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the porous polymeric particles, the polymeric binder, and an optional precipitation agent (for example, a pH adjusting agent such as alum) can be added to the slurry.

When the wetlaid process is carried out by using handsheet methods known in the art, the order of addition of the three components (i.e., fibers, polymeric binder, and porous polymeric particles) to the dispersion has not been found to significantly affect the ultimate performance of the concentration device. If the polymeric binder is a latex, it may be preferable to add the polymeric binder after addition of the porous polymeric particles. This later addition can improve adhesion of the porous polymeric particles to the fibers of the porous matrix. For some other polymeric binders, it may be preferable to add them to the porous matrix prior to addition of the porous polymeric particles. The choice and amount of the polymeric binder must be selected with care to avoid blocking the pores of the porous polymeric particles with the polymeric binder.

After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 100° C. to 150° C., or in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or up to 99 weight percent of the dispersing liquid based on the amount of dispersing liquid added to form the dispersion). When polymeric binder fibers are used as the polymeric binder in the wetlaid process, a precipitation agent is typically not needed and the applied heat can be used to melt the polymeric binder fibers.

The resulting porous article is a dry sheet having an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or up to 10 millimeters. Calendering can be used to provide additional pressing or fusing, if desired, of the dry sheet.

In the porous article, the porous polymeric particles can be entrapped in the fibrous porous matrix through either chemical interactions (for example, chemical bonding) or physical interactions (for example, adsorption or mechanical entrapment), depending upon the nature of the fibers that are utilized. The porous polymeric particles are often preferably distributed essentially uniformly throughout the fibrous porous matrix within the porous article.

Generally the average pore size of the dry porous article can be in a range of 0.1 to 10 micrometers, as measured by scanning electron microscopy (SEM). Void volumes in the range of 20 to 80 volume percent or in a range of 40 to 60 volume percent can be useful. The porosity of the dry porous article can be modified (increased) by using fibers of larger diameter or stiffness in the fiber mixture.

The porous article can be flexible (for example, it can be a porous sheet rolled around a 0.75 inch (about 2 cm) diameter core). This flexibility can enable the sheet to be pleated or rolled. The porous sheet has an open pore structure that tends to provide minimal resistance to the passage of samples (e.g., a fluid stream such as a liquid sample). Because of this minimal resistance, relatively high volumes of liquid can be relatively quickly passed through it without generating a relatively high back pressure.

The uncalendered porous sheet can be cut to a desired size and used in a separation device. If desired (for example, when a significant pressure drop across the sheet is not a concern), the porous sheet can be calendered to increase its tensile strength prior to use. When the porous article is to be pleated, drying and calendering are typically avoided.

The porous article can be used to separate a target material from a sample. For example, the porous article can be used to concentrate a microorganism (i.e., cellular analyte) from a sample. Any method can be used to contact the porous article with the sample. For example, the porous article can be immersed in a sample, a sample can be poured over the porous article, the sample can be poured into a tube or well containing the porous article, or the sample can be passed over or through the porous article. Preferably, the sample is contacted with the porous article in a manner such that the sample contacts the porous polymeric particles distributed throughout the porous article.

In a third aspect, a separation device is provided. The separation device includes a) a container having an inlet and an outlet for passage of a fluid stream through the container and b) a porous article positioned within the container. The porous article is the same as described above. Any suitable container can be used. Both the container and the porous article can have any desired size. In many embodiments, the porous article fills at least 25 volume percent, at least 50 volume percent, or at least 75 volume percent of the container.

In some embodiments, the container is a column or cartridge (for example, a filter cartridge) containing the porous article. The fluid stream enters into a first end of the column or cartridge and exits through a second end of the column or cartridge. While in the column or cartridge, the fluid stream contacts the porous article. In one example, the separation device is in the form of filter such as a syringe filter. The sample is placed in the syringe and then passed through the filter containing the porous article. In any of the separation devices, the fluid stream can pass over the porous article, through the porous article, or both. The filter can contain one or more sheets of the porous article. Multiple layers of the porous sheet can be used to provide greater binding capacity for the target material. The amount of porous article included in the separation device is often selected to be sufficient to separate (for example, capture or concentrate) the target material of a particular sample.

If desired, the separation device can further contain one or more other components such as, for example, one or more pre-filters (for example, to remove relatively large food particles from a sample prior to passage of the sample through the porous article), a support or base for the porous article (for example, in the form of a frit or grid), or a manifold for applying a pressure differential across the separation device (for example, to aid in passing a sample through the porous article).

If desired, the separation device can be sterilized (for example, by controlled heat, ethylene oxide gas, or radiation) prior to use, in order to reduce or prevent any contamination of the sample that might cause detection errors. This is particularly useful when the target material is a microorganism.

Any suitable sample can be introduced into the separation device. The composition of the porous polymeric particles within the porous article included in the separation device can be altered to capture the desired type of target material. In some embodiments, the porous polymeric particle composition is selected to capture microorganisms from a sample. In this embodiment, the monomers used to form the porous polymeric particles typically do not contain an ionic group. Alternatively, less than 1 weight percent, less than 0.5 weight percent, or less than 0.1 weight percent of the monomers in the monomer composition are ionic monomers.

When the target material is a microorganism, the microorganism is captured by the porous article within the separation device. The microorganism may be present in a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is a fluid (for example, a liquid or a dispersion of a solid in a liquid, or dispersion of a first liquid in a second liquid).

Specific examples of samples include foods (for example, fresh produce, ground meat), beverages (for example, juices or carbonated beverages), water (including potable water), and biological fluids. Biological fluids include, for example, whole blood or a component thereof (for example, plasma, a platelet-enriched blood fraction, a platelet concentrate, or packed red blood cells) cell preparations (for example, dispersed tissue, bone marrow aspirates, or vertebral body bone marrow), cell suspensions, urine, saliva, bone marrow, lung fluid, cerebral fluid, wound exudates, wound biopsy samples, ocular fluid, spinal fluid, and lysed preparations (for example, cell lysates, which can be formed using known procedures such as the use of lysing buffers).

Microorganisms can be separated from a sample in a concentrated state. In some embodiments, the microorganisms can be separated from other sample components that can inhibit detection of the microorganisms. Optimally, if additional concentration is desired, cultures can be grown from samples either before or after passage of the sample through the separation device. Such cultural enrichment can be general or primary (so as to enrich the concentrations of most or essentially all microorganisms) or can be specific or selective (so as to enrich the concentration(s) of one or more selected microorganisms only).

The sample volume can vary depending upon the particular application. For example, when the sample is for diagnostic or research applications, the volume of the sample can typically be in the microliter range (for example, 10 microliters or greater). When the sample is for food pathogen testing assay or for potable water safety testing, the volume of the sample can typically be in the milliliter to liter range (for example, 100 milliliters to 3 liters). In an industrial application, such as bioprocessing or pharmaceutical formulation or for the purification of a liquid such as drinking water, the volume can be tens of thousands of liters.

The sample can contact the porous article within the separation device for any desired time period. In some embodiments, the contact time is from about 10 seconds to about 60 minutes depending on the size of the sample. Contact between the porous article and the sample can be enhanced by mixing (for example, by shaking the separation device or by addition of a stirrer within the container of the separation device) or by application of a pressure differential across the separation device to facilitate passage of a sample through its porous article) and/or by incubation (for example, at ambient temperature).

In a fourth aspect, a system is provided. The system includes a separation device that includes a) a container having an inlet and an outlet and b) a porous article positioned within the container. The porous article is the same as described. The system further includes a fluid stream passing through the separation device, wherein the fluid stream enters the inlet and exits the outlet of the container and contacts the porous article positioned within the container.

Any method can be used to provide the fluid stream through the separation device. In some embodiments, the system includes a pump to provide the fluid stream. Essentially any type of pump (for example, a peristaltic pump) can be used. In other embodiments, other equipment can be used to establish a pressure differential across the separation device. For example, a syringe or plunger can be used. Useful flow rates will vary depending upon such factors as the nature of the sample and the particular application. For example, flow rates of the fluid stream through the separation device of about 100 milliliters per minute or more can be effective. Longer contact times and slower flow rates can be useful for more complex samples. For many samples, flow rates in a range of 1 to 100 milliliters per minute, in a range of 1 to 50 milliliters per minute, or in a range of 1 to 20 milliliters per minute can be utilized. For pre-filtered or otherwise clarified food samples, flow rates of about 6 milliliters per minute (1.5 milliliters per 15 seconds) can be useful.

The contact time, flow rate, and amount of the porous article included in the separation device, and the amount of porous polymeric particles included in the porous article can all impact the removal efficiency of the separation device for the target material. In embodiments where the target material is a microorganism, the percent removal of the microorganisms from a sample can be at least 90 percent, at least 95 percent, at least 98 percent, or at least 99 percent.

One or more optional additives can be contacted with the porous article after passage of a fluid stream through the separation device. Any suitable method of contacting the porous article with the optional additives can be used. Methods include, for example, passing the optional additive through the porous article while it is positioned within the separation device. Alternatively, the porous article can be removed from the separation device or the entire separation device can be placed within the optional additive. Optional additives include, for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, TRITON X-100 nonionic surfactant available from Dow Chemical, Houston, Tex.), mechanical abrasion/elution agents (for example, glass beads), and buffers.

In a fifth aspect, a method of separating a target material is provided. The method includes providing a separation device. The separation device includes a container having an inlet and an outlet. The porous article is the same as described above. The method further includes passing a fluid stream comprising a target material through the separation device, wherein the fluid stream enters the inlet and exits the outlet of the container and contacts the porous article positioned within the container. The method still further includes removing the target material from the fluid stream, wherein the target material is bound (for example, chemically or physically adsorbed) or captured by the porous article.

The target material is bound or captured by the porous article as the fluid stream of the sample is passed through the separation device. The mechanism of separating (removing) the target material may vary depending on the composition of the porous polymeric material within the porous article, the size of the pores within the porous polymeric material, as well as the size and/or the structure of the target material.

In some embodiments, the target material is a microorganism. For the capture of microorganisms as the target material, the porous polymeric material typically does not have ionic groups such as sulfonic acid groups or salts thereof, carboxylic acid groups or salts thereof, and/or quaternary ammonium groups. Microorganisms are often comparable in size or smaller in size than the porous polymeric particles. In this sense, it is surprising that microorganisms can be separated from samples using the porous articles described herein. While not wishing to be bound by theory, lipids that typically accompany microorganisms may be sorbed by the porous polymeric particles resulting in the simultaneous capture of microorganisms. The microorganisms themselves probably do not enter the pores of the porous polymeric particles because they are usually considerably larger than the pores; however, a portion of a microorganism may be bound within a pore of the porous polymeric particle.

The purpose for removing the target material from the fluid stream or sample can vary. In some embodiments, the removal of the target material is for purification purposes. For target materials that are microorganisms, the separation device can be used to provide a purified fluid stream. For example, the fluid stream can be water that may contain microorganisms that are removed by the porous article within the separation device. In other embodiments, the removal of the target material is for the purpose of detecting the presence of the target material. The separation device removes the target material (e.g., a microorganism) from the fluid stream and concentrates the target material on the porous article within the separation device.

The method of separating the target material may further include isolating or removing the captured target material from the porous article. In the embodiment where the target material is a microorganism, the captured microorganism can be removed from the porous article, for example by passing an elution agent over or through the separation device.

Any of the steps in the method of separating a target material can be carried out manually (for example, in a batch-wise manner) or can be automated (for example, to enable continuous or semi-continuous processing).

A variety of microorganisms can be concentrated using the separation device described herein. Suitable microorganisms can be, for example, bacteria (including both gram-negative bacteria and gram positive bacteria), fungi, yeasts, molds, protozoans, viruses (including both non-enveloped and enveloped viruses), bacterial endospores (for example, *Bacillus* (including *Bacillus anthracis*, *Bacillus cereus*, and *Bacillus subtilis*) and *Clostridium* (including *Clostridium botulinum*, *Clostridium difficile*, and *Clostridium perfringens*)), and combinations thereof. The microorganisms can be subsequently detected. The separation and detection of microorganisms can be particularly important for food safety or for medical, environmental, or anti-terrorism reasons.

Genera of microorganisms to be separated and detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof. Samples can contain a plurality of microorganism strains, and any one strain can be detected independently of any other strain. Specific microorganism strains that can be targets for separation and detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracis, Bacillus atrophaeus, Bacillus subtilis, Clostridium perfringens, Clostridium botulinum, Clostridium difficile, Enterobacter sakazakii*, human-infecting non-enveloped enteric viruses, *Pseudomonas aeruginosa*, and the like, and combinations thereof. In some embodiments, the microorganism strains are *Listeria monocytogenes, Escherichia coli, Salmonella enterica, Staphylococcal enterotoxin* ssp, and combinations thereof.

Microorganisms that have been captured or bound on the porous article of the separation device can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample components, slicing or otherwise breaking up the porous article of the separation device, staining, boiling or using elution buffers or lysis agents to release microorganisms from the concentration device, or the like. The detection methods often depend on the viability of the microorganism. Removal of microorganisms by the porous article typically does not adversely affect their viability.

As used herein, the term "viability" in reference to a microorganism means that the microorganism is capable of replicating for at least the amount of time needed for detection of the microorganism.

Immunological detection is detection of an antigenic material derived from a target microorganism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.), the descriptions of which are incorporated herein by reference. Other luminescence-based detection methods can also be utilized.

Since the process of the invention is non-strain specific, it provides a general capture system that allows for multiple microorganism strains to be targeted for assay in the same sample. For example, in assaying for contamination of food samples, it can be desired to test for *Listeria monocytogenes, Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Various embodiments are provided that include a porous article, a method of making a porous article, a separation device, a system, and a method of separating a target material.

Embodiment 1 is a porous article that includes a) porous polymeric particles and b) a fibrous porous matrix, wherein the porous polymeric particles are distributed throughout the fibrous porous matrix. The porous polymeric particles include a polymerized product of a reaction mixture that contains i) a monomer composition and ii) a poly(propylene glycol) having a weight average molecular weight of at least 500 grams/mole. The monomer composition contains at least 10 weight percent of a first monomer of Formula (I)

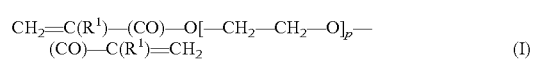

based on a total weight of the monomer composition. In Formula (I), the variable p is an integer equal to at least 1 and $R^1$ is hydrogen or alkyl. The poly(propylene glycol) is removed from the polymerized product to provide the porous polymeric particles.

Embodiment 2 is the porous article of embodiment 1, wherein the fibrous porous matrix comprises nonwoven fibers.

Embodiment 3 in the porous article of embodiment 1 or 2, wherein the reaction mixture used to form the porous polymeric particles includes (a) a first phase and (b) a second phase dispersed in the first phase, wherein a volume of the first phase is greater than a volume of the second phase. The first phase contains (i) a compound of Formula (II)

$$HO[CH_2-CH(OH)-CH_2-O]_n-H \qquad (II)$$

where the variable n is an integer equal to at least 1 and (ii) a nonionic surfactant. The second phase contains (i) a monomer composition comprising the monomer of Formula (I)

$$CH_2=C(R^1)-(CO)-O[-CH_2-CH_2-O]_p-\\(CO)-C(R^1)=CH_2 \qquad (I)$$

where the variable p is an integer equal to at least 1 and where $R^1$ is hydrogen or methyl, and (ii) a poly(propylene glycol) having a weight average molecular weight of at least 500 grams/mole. The poly(propylene glycol) is removed from the polymerized product to provide the porous polymeric particles.

Embodiment 4 is the porous article of any one of embodiments 1 to 3, wherein the monomer composition further comprises a second monomer having one (meth)acryloyl group.

Embodiment 5 is the porous article of any one of embodiments 1 to 3, wherein the monomer composition further comprises a second monomer of Formula (III) of Formula (IV).

$$CH_2=CR^1-(CO)-O-Y-R^2 \qquad (III)$$

$$CH_2=CR^1-(CO)-O-R^3 \qquad (IV)$$

The group $R^1$ is hydrogen or methyl. The group Y is a single bond, alkylene, oxyalkylene, or poly(oxyalkylene). Group $R^2$ is a carbocyclic group or heterocyclic group. Group $R^3$ is a linear or branched alkyl.

Embodiment 6 is the porous article of any one of embodiments 1 to 3, wherein the monomer composition further comprises a second monomer that is a hydroxyl-containing monomer of Formula (V) or Formula (VI).

$$CH_2=CR^1-(CO)-O-R^4 \qquad (V)$$

$$CH_2=CR^1-(CO)-O-R^5-O-Ar \qquad (VI)$$

The group $R^1$ is hydrogen or methyl. The group $R^4$ is an alkyl substituted with one or more hydroxyl groups or is a group of formula $-(CH_2CH_2O)_qCH_2CH_2OH$ where q is an integer equal to at least 1. The group $R^5$ is an alkylene substituted with at least one hydroxyl group and the group Ar is an aryl group.

Embodiment 7 is the porous article of any one of embodiments 1 to 3, wherein the monomer composition further comprises a second monomer having an ionic group.

Embodiment 8 is the porous article of any one of embodiments 1 to 7, wherein the fibrous porous matrix comprises polymeric fibers.

Embodiment 9 is the porous article of embodiment 8, wherein the polymeric fibers comprise a polyamide, a polyolefin, a polysulfone, or a combination thereof.

Embodiment 10 is the porous article of embodiment 8 or 9, wherein the fibrous porous matrix comprises a fibrillated polyolefin polymeric fiber.

Embodiment 11 is the porous article of any one of embodiments 8 to 10, wherein the fibrous porous matrix further comprises inorganic fibers.

Embodiment 12 is the porous article of embodiment 11, wherein the inorganic fibers comprise glass fibers, ceramic fibers, or a combination thereof.

Embodiment 13 is the porous article of any one of embodiments 1 to 12, wherein the fibrous porous matrix further comprises a polymeric binder.

Embodiment 14 is the porous article of any one of embodiments 1 to 12, wherein the porous article comprises 10 to 55 weight percent porous polymeric particles based on a total dried weight of the porous article and 45 to 90 weight percent fibrous porous matrix based on the total dried weight of the porous article.

Embodiment 15 is the porous article of any one of embodiments 1 to 12, wherein the porous article comprises 20 to 50 weight percent porous polymeric particles based on a total dried weight of the porous article and 50 to 80 weight percent fibrous porous matrix based on the total dried weight of the porous article.

Embodiment 16 is the porous article of any one of embodiments 1 to 15, wherein the fibrous porous matrix is a nonwoven fibrous layer comprising a plurality of polymeric fibers, inorganic fibers, or a combination thereof.

Embodiment 17 is the porous article of any one of embodiments 1 to 15, wherein the fibrous porous matrix is a nonwoven fibrous layer and the porous polymeric particles are enmeshed in the nonwoven fibrous layer.

Embodiment 18 is the porous article of embodiment 17, wherein the nonwoven fibrous layer comprises polyolefin fibers, polyamide fibers, and glass fibers.

Embodiment 19 is the porous article of any one of embodiments 1 to 18, wherein the porous polymeric particles are in the form of beads.

Embodiment 20 is a method of making a porous article. The method includes a) providing a plurality of porous polymeric particles and b) distributing the porous polymeric particles throughout a fibrous porous matrix. The porous polymeric particles include a polymerized product of a reaction mixture that contains i) a monomer composition and ii) a poly(propylene glycol) having a weight average molecular weight of at least 500 grams/mole. The monomer composition contains at least 10 weight percent of a first monomer of Formula (I)

$$CH_2=C(R^1)-(CO)-O[-CH_2-CH_2-O]_p-\\(CO)-C(R^1)=CH_2 \qquad (I)$$

based on a total weight of the monomer composition. In Formula (I), the variable p is an integer equal to at least 1 and $R^1$ is hydrogen or alkyl. The poly(propylene glycol) is removed from the polymerized product to provide the porous polymeric particles.

Embodiment 21 is the method of embodiment 20, wherein the reaction mixture contains 1) a first phase having a first volume and 2) a second phase having a second volume and being dispersed in the first phase, wherein the first volume is greater than the second volume. The first phase contains i) a compound of Formula (II) and ii) a nonionic surfactant.

$$HO(-CH_2CH(OH)CH_2O)_n \qquad (II)$$

In Formula (II), the variable n is an integer equal to at least 1. The second phase contains i) the monomer composition comprising at least 10 weight percent of the monomer of Formula (I) based on the total weight of the monomer composition; and ii) the poly(propylene glycol) having a weight average molecular weight of at least 500 grams/mole. The poly(propylene glycol) is removed from the polymerized product to provide the porous polymeric particle.

Embodiment 22 is the method of embodiment 20 or 21, wherein the fibrous porous matrix is a nonwoven fibrous layer comprising a plurality of polymeric fibers, inorganic fibers, or a combination thereof and wherein the porous polymeric particles are enmeshed in the nonwoven fibrous layer.

Embodiment 23 is the method of any one of embodiments 20 to 22, wherein the porous article comprises 10 to 55 weight percent porous polymeric particles based on a total dried weight of the porous article and 45 to 90 weight percent fibrous porous matrix based on the total dried weight of the porous article.

Embodiment 24 is a separation device that includes a) a container having an inlet and an outlet for passage of a fluid stream through the container and b) a porous article of any one of claims 1 to 19 positioned within the container.

Embodiment 25 is a system that includes a) a separation device and b) a fluid stream passing through the separation device, wherein the fluid stream enters the inlet and exits the outlet of the container and contacts the porous article positioned within the container. The separation device includes a) a container having an inlet and an outlet for passage of a fluid stream through the container and b) a porous article of any one of claims 1 to 19 positioned within the container.

Embodiment 26 is the system of embodiment 25, wherein the fluid stream comprises a target material and wherein the porous article removes the target material from the fluid stream.

Embodiment 27 is the system of embodiment 26, wherein the target material comprises a microorganism.

Embodiment 28 is the system of embodiment 27, wherein the fluid stream further comprises a lipid.

Embodiment 29 is the system of embodiment 27 or 28, wherein the microorganism that is removed by the porous article remains viable for detection or assay of the microorganism.

Embodiment 30 is the system of any one of embodiments 27 to 29, wherein the microorganism comprises a bacteria, fungi, yeast, protozoan, virus, bacterial endospore, components thereof, or combinations thereof.

Embodiment 31 is a method of separating a target material. The method includes providing a separation device. The separation device includes a container having an inlet and an outlet. The porous article is the same as described above. The method further includes passing a fluid stream comprising a target material through the separation device, wherein the fluid stream enters the inlet and exits the outlet of the container and contacts the porous article positioned within the container. The method still further includes removing the target material from the fluid stream, wherein the target material is bound or captured by the porous article. In some embodiments of the fifth aspect, the target material is a microorganism.

Embodiment 32 is the method of embodiment 31, wherein the target material comprises a microorganism.

Embodiment 33 is the method of embodiment 32, wherein the fluid stream further comprises a lipid.

Embodiment 34 is the method of embodiment 31 or 32, wherein the microorganism is viable after being bound or captured by the porous article.

Embodiment 35 is the method of any one of embodiments 31 to 34, wherein the microorganism comprises a bacteria, fungi, yeast, protozoan, virus, bacterial endospore, components thereof, or combinations thereof.

Embodiment 36 is the method of any one of embodiments 31 to 35, further comprising detecting the amount of microorganism bound or captured by the porous article.

Embodiment 37 is the method of any one of embodiments 31 to 36, wherein removing the target material purifies the fluid stream.

EXAMPLES

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

TABLE 1

Materials and Articles Used in Examples

| Material | Description |
| --- | --- |
| SR 339 | Trade designation for 2-phenoxyethyl acrylate ester monomer, which was obtained from Sartomer Company, Inc. (Exton, PA, USA) |
| SR 603 | Trade designation for polyethylene glycol (400) dimethacrylate monomer with a weight average molecular weight of 400 grams/mole, which was obtained from Sartomer Company, Inc. (Exton, PA, USA) |
| PPG | Polypropylene glycol having a weight average molecular weight of 4000 grams/mole, which was obtained from Alfa Aesar (Ward Hill, MA, USA) |
| IRGACURE 819 | Trade designation for the photoinitiator bis-(2,4,6-trimethylbenzoyl)-phenylphosphine oxide, which was obtained from BASF (Florham Park, NJ, USA) |
| APG 325 N | Trade designation for a nonionic alkyl polyglucoside surfactant, which was obtained from Cognis Corporation (Cincinnati, OH, USA) |
| IPA | Isopropyl alcohol, which was obtained from Sigma-Aldrich Corp. (St. Louis, MO, USA) |
| Fiber 1 | Short fibrillated polyethylene fibers commercially available under the trade designation "SHORT STUFF POLYETHYLENE" from Minifibers, Inc. (Johnson City, TN, USA) |
| Fiber 2 | Chopped nylon fibers having a length of ½ inch and a linear mass density of 1 deniers that were obtained from Minifibers, Inc. (Johnson City, TN, USA) |
| Fiber 3 | Bi-component (ethylene vinyl acetate and polypropylene) fibers with a length of 5 millimeter and a linear mass density of 2 deniers that were obtained from Minifibers, Inc. (Johnson City, TN, USA). |

TABLE 1-continued

Materials and Articles Used in Examples

| Material | Description |
| --- | --- |
| Fiber 4 | Glass fibers commercially available under the trade designation MICRO-STRAND 106-475 from Schuller Inc. (Denver, CO, USA). |
| DI Water | Deionized water with a resistivity of 18 megaohms that passed through a purification system commercially available under the trade designation MILLI-Q GRADIENT SYSTEM from Millipore (Waltham, MA, USA). |
| Butterfield's Buffer | A monobasic potassium phosphate buffer solution having a pH equal to 7.2 ± 0.2 that can be purchased (Catalog# FTBFD90) from 3M Company (Saint Paul, MN, USA) |
| Tryptic Soy Agar Plate | A plate prepared according to manufacturer's instructions using 3 weight percent DIFCO Tryptic Soy Agar. The DIFCO Typtic Soy Agar can be purchased from Benton Dickinson (Sparks, MD, USA) |
| Tryptic Soy Broth | Broth prepared according to manufacturer's instructions using 3.7 weight percent DIFCO Tryptic Soy Broth powder, which can be purchased from Benton Dickinson (Sparks, MD, USA) |
| MOX Plate | A plate prepared using Oxford Medium modified for *Listeria* that is commercially available from Hardy Diagnostics (Santa Maria, CA, USA) |
| *E. coli* Plate | A plate commercially available under the trade designation 3M *E. COLI*/COLIFORM PETRIFILM PLATE from 3M Company (Saint Paul, MN, USA) |
| Syringe | A syringe having a tip that is commercially available under the trade designation "BD LUER-LOK" that can be purchased from VWR (West Chester, PA, USA) |
| Filter Holder | A 13 millimeter filter holder that is commercially available under the trade designation SWINNEX from Millipore Corp. (Bedford, MA, USA) |
| Stomacher | A blender commercially available under the trade designation STOMACHER 400 Circulator Laboratory Blender that can be purchased from VWR (West Chester, PA, USA) |
| Stomacher Bag | A polyethylene sample bag commercially available under the trade designation FILTRA-BAG that can be purchased from VWR (West Chester, PA, USA) |
| *E. coli* | *Escherichia coli* ATCC 11229 that was purchased from American Type Culture Collection (Manassas, VA, USA) |
| *L. monocytogenes* | *Listeria monocytogenes* ATCC 51414 purchased from American Type Culture Collection (Manassas, VA, USA) |

Preparatory Example 1: Preparation of Porous Polymeric Particles

The monomers SR 339 (50 grams) and SR 603 (50 grams) were mixed with PPG (43 grams) and IRGACURE 819 (250 milligrams). The mixture was stirred vigorously for 20 minutes while heating in a range of about 40° C. to 50° C. This mixture was then added to 750 grams of glycerol previously mixed with 7.5 grams of the surfactant APG 325 N. The mixture was shear mixed for 20 minutes. The mixture was then spread thin between two sheets of polyethylene terephthalate film (which can be obtained from DuPont, Wilmington, Del., under the trade designation "MELINEX ST 500"). The mixture was cured with ultraviolet light for 15 to 20 minutes with a 100 Watts, long-wavelength BLACK RAY UV lamp (obtained from UVP, LLC, Upland, Calif.) situated at about 15 centimeters from the surface of the curing material.

The cured mixture was then dispersed in excess water (500 mL), shaken for 30 minutes, and centrifuged at 3000 rpm in an EPPENDORF 5810 R centrifuge (obtained from Eppendorf, Germany). The supernatant was removed and the resulting particles were then re-suspended in 500 mL of water for a second rinse followed by centrifugation. After this, the particles were suspended in a 500 mL IPA and shaken for 20 minutes. This shaking in IPA extracted the PPG and left voids (i.e., pores or free volume) in the particles. The particles were then centrifuged at 300 rpm for 30 minutes and the supernatant was discarded. The void volume seen in FIG. 1 (i.e., pore volume) in the particles is expected to be equivalent to the volume of PPG removed.

Examples 1-2 and Comparative Example 1: Preparation of Porous Articles

Three fiber premixes were prepared by mixing various amounts of Fiber 1 and Fiber 2, Fiber 3, and Fiber 4 as shown in Table 2 below. Fiber 1 was added to 3 liters of cold deionized water in a 4 L blender (commercially available from VWR (Radnor, Pa., USA) under the trade designation "WARING COMMERCIAL HEAVY DUTY BLENDER, MODEL 37BL84") and blended at medium speed for 30 seconds. The mixture was examined for uniform dispersion of the fibers without nits or clumps. Fibers 2, 3 and 4 were added and the mixture was blended further for 15 seconds on low speed to break up clumps. The porous polymeric particles from Preparatory Example 1 were added to Examples 1 and 2 with an additional liter of deionized water and mixed at low speed for 15 seconds. Comparative Example 1 did not contain porous polymeric particles.

A felt was prepared using a pad maker apparatus (obtained from Williams Apparatus, Watertown, N.Y., under the trade designation "TAPPI") that had a box measuring about 30 centimeters (12 inches) square and (12 inches) high with a fine mesh screen at the bottom and a drain valve. On the screen was laid a piece of polyethylene spunbound (PET LUTRADUR 7240 obtained from Fiberweb, Cincinnati, Ohio, USA) having dimensions of about 35.6 centimeters (14 inches) by 30 centimeters (12 inches) as the scrim on the screen. The box was filled with tap water up to a height of about 1 centimeter above the screen. The fiber and nanoporous microparticle (porous polymeric particle) mixture was poured into the box and the valve was opened immediately which created a vacuum that pulled the water out of the box. The resulting wet-laid felt was approximately 0.8-1 millimeter thick.

The wet-laid felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 2.5 hrs to remove residual water and to form a porous wet-laid matrix.

TABLE 2

Composition of Examples 1-2 and Comparative Example 1

| Material | Example 1 (grams) | Example 2 (grams) | Comparative Example 1 (grams) |
|---|---|---|---|
| Fiber 1 | 11.04 | 11.01 | 11.02 |
| Fiber 2 | 3.01 | 3.01 | 3.01 |
| Fiber 3 | 2.27 | 2.27 | 2.25 |
| Fiber 4 | 1.75 | 1.75 | 1.74 |
| Porous Polymeric Particles of Preparatory Example 1 | 10.00 | 17.00 | 0.00 |

Examples 3-5 and Comparative Example 2: Removal of Bacteria from Potable Water A streaked culture of *E. coli* on a Tryptic Soy Agar plate was incubated overnight at 37° C. From this plate an isolated colony was removed and inoculated into 10 mL of Tryptic Soy Broth using a standard microbiology loop and incubated in a shaking incubator (INNOVA 44 from New Brunswick Scientific) at 37° C. for 20 to 22 hours. The overnight culture that contained approximately $2-3 \times 10^9$ CFU/mL was serially diluted in Butterfield's Buffer to obtain an inoculum with approximately $1 \times 10^6$ CFU/mL.

A pre-filtration sample was prepared by inoculating 200 mL DI water (MilliQ Gradient system, Millipore, Ma) with a 1:100 dilution of the $10^6$ CFU/mL inoculum resulting in water test sample containing approximately $10^4$ CFU/mL (about 4 Log CFUs/ml).

Example 3

A disk 47 millimeters in diameter was die punched from the porous article of Example 1 and placed into a disk holder, which was a custom fabricated from polycarbonate. The disk holder had three parts and was cylindrically shaped measuring about 60 millimeters in diameter by about 45 millimeters high. The lower part contained a support screen for the porous article disk and a sample outlet port. The top portion was enclosed except for the sample inlet port through polyvinyl chloride (PVC) tubing connected to the Cole Parmer peristaltic pump and a vent on the upstream side to allow for purging air. O-ring seals were used to prevent leakage on both the upstream and downstream sides. Internal threads provided closure pressure. The 47 millimeter porous article disk was placed on top of the support screen, an O-ring was added on top of the disk, and holder was closed to prepare a separation device.

The porous article was tested in duplicates. A pre-filtration sample was pumped through the separation device containing the nonwoven porous article disk at a flow rate of 12 ml/minute with a Cole Parmer peristaltic pump (Model No. 7553-70) using ⅛" wall thick PVC tubing (VWR catalog #60985-522). Filtrates were collected in 250 mL sterile glass bottles. The first 100 mL filtrate was collected and discarded. The second 100 mL filtrate was collected for further processing.

After each filtration test, the separation device was disassembled to remove the nonwoven porous article using sterile forceps. Between testing of the nonwoven porous articles, the disk holder was rinsed with filtered and sterilized 500 mL deionized water.

A 1 mL volume of the second 100 mL filtrate was added to a tube containing 9 mL Butterfield's buffer to obtain a 1:10 dilution. The tube was capped and mixed manually by shaking for 10 seconds. A 1 mL volume was removed and added to another tube containing 9 mL Butterfield's buffer to obtain a 1:100 dilution. Similarly the filtrate was further diluted to 1:1000 and 1:10000. One mL volume was plated on *E. coli* plates in duplicates per dilution.

The plates were incubated at 37° C. for 18-20 hours per manufacturer's instructions. Colony counts were obtained by reading the plates in the PETRIFILM PLATE READER (from 3M Company (Saint Paul, Minn., USA)). Pre-filtration samples were also diluted and plated using the same procedure. The CFU/mL colony counts were converted to Log CFU/mL values. The Log Reduction Value (LRV) was calculated based on counts obtained from the plated filtrate and plated pre-filtration sample using Equation (A). The results are shown in Table 3.

LRV=(Log of CFUs/mL in pre-filtration sample)– (Log of CFUs/mL in filtrate sample).  Equation (A):

Example 4

Example 4 tested as in Example 3 except two 47 millimeter porous article disks of Example 1 were used. The results are shown in Table 3.

Example 5

Example 5 was tested as in Example 3 except that two 47 millimeter porous article disks of Example 2 were used. The flow rate was 70 mL/min and the pre-filtration sample was 100 mL. The results are shown in Table 3.

Comparative Example 2

Comparative Example 2 was tested as in Example 3 except that two 47 mm disks of Comparative Example 1 were used. The flow rate was 70 mL/min and the pre-filtration sample was 100 mL. Results are shown in Table 3.

TABLE 3

Efficiency of removal of bacteria from potable water

| Filtration Example # | Porous Article or Matrix Example # | Flow Rate (mL/min) | Log CFUs in Pre-Filtration Sample | LRV |
|---|---|---|---|---|
| 3 | 1 | 12 | 4.29 | 0.53 |
| 4 | 1 | 12 | 4.29 | 1.51 |
| 5 | 2 | 70 | 4.22 | 1.28 |
| CE-2 | CE-1 | 70 | 4.22 | 0.98 |

Examples 6-7: Removal of *E. coli* from Ground Meat Samples

Ground meat (beef and turkey) was purchased from local grocery store.

An 11 gram sample of ground beef (15% fat) was added a sterile stomacher bag and blended with 99 mL Butterfield's buffer solution in a STOMACHER 400 CIRCULATOR laboratory blender for a 30 second cycle at 230 rpm speed to generate a blended ground beef sample matrix.

A single colony of E. coli from an overnight streak culture on a Tryptic Soy Agar plate was inoculated into 10 mL of Tryptic Soy Broth and incubated at 37° C. in a shaker incubator (INNOVA44 from New Brunswick Scientific) for 18 to 20 hours. The resulting bacterial stock containing approximately $1 \times 10^9$ CFU/mL was serially diluted in Butterfield's buffer to obtain an approximately $1 \times 10^5$ CFU/mL inoculum (E. coli suspension), which was inoculated in the blended ground beef sample to obtain a "spiked beef sample" having approximately $1 \times 10^3$ CFU/mL.

A "spiked ground turkey sample" was prepared using the same procedure except that a ground turkey matrix was used.

Example 6

A disk 14 millimeter in diameter was die punched from the porous article of Example 1 and placed into a 13 millimeter SWINNEX holder (purchased from Millipore (Waltham, Mass., USA). The porous article was tested in duplicates. A 1 mL volume of the spiked ground beef was filtered through the porous article disk using a syringe.

Filtrates were collected in 1.5 mL sterile polypropylene microfuge tubes. A 100 microliter volume was added to 900 microliters Butterfield's buffer to obtain a 1:10 dilution. After mixing, a 100 microliter volume was added to 900 microliters Butterfield's buffer to obtain a 1:100 dilution. Filtrates from the ground beef sample were plated on E. coli plates neat (undiluted). Filtrates from the ground turkey sample were plated on E. coli plates at 1:10 and 1:100 dilutions. The plates were incubated at 37° C. for 18-20 hours per manufacturer's instructions. Colony counts were obtained by reading the plates in the PETRIFILM PLATE READER (from 3M Company). Pre-filtration (spiked ground meat) samples were also diluted, plated and read as the procedure above. The pre-filtration ground beef sample had an average colony count of 3950 CFU/mL.

Capture efficiency was calculated based on colony counts obtained from the plated filtrate and plated pre-filtration sample using Equations B and C. The results are in Table 4.

% Control=(Colony counts from plated filtrate/
Colony counts from pre-filtration sample)×100     Equation B:

Capture Efficiency or % Capture=100−% Control     Equation C:

Example 7

A disk 14 mm in diameter was die punched from the wet-laid of Example 2 and placed into a 13 mm SWINNEX holder (purchased from Millipore, Waltham, Mass.). The wet-laid was tested in duplicates. A 1 mL volume of the spiked ground turkey was filtered thru the wet-laid disk using a syringe.

Filtrates were collected in 1.5 mL sterile polypropylene microfuge tubes. A 100 microliter volume was added to 900 microliters Butterfield's buffer to obtain a 1:10 dilution. After mixing, a 100 microliter volume was added to 900 microliters Butterfield's buffer to obtain a 1:100 dilution. Filtrates from the ground turkey sample were plated on E. coli plates at 1:10 and 1:100 dilutions. The plates were incubated at 37° C. for 18-20 hours per manufacturer's instructions. Colony counts were obtained by reading the plates in the PETRIFILM PLATE READER (from 3M Company). Pre-filtration (spiked ground meat) samples were also diluted, plated and read as the procedure above. The pre-filtration ground turkey sample had an average colony count of 3100 CFU/mL.

Capture efficiency was calculated based on colony counts obtained from the plated filtrate and plated pre-filtration sample using Equations B and C. The results are in Table 4.

TABLE 4

Efficiency of removal of E. coli from ground meat samples

| Filtration Example # | Porous Article Example # | % Capture |
|---|---|---|
| 6 | 1 | 99 |
| 7 | 1 | 98 |

Example 8 and Comparative Example 3: Removal of L. monocytogenes from Ground Beef Ground beef was purchased from local grocery store. An 11 gram sample of ground beef (15% fat) was added a sterile stomacher bag and blended with 99 mL Butterfield's buffer solution in a STOMACHER 400 CIRCULATOR laboratory blender for a 30 second cycle at 230 rpm speed to generate a blended ground beef sample matrix.

A single colony of L. monocytogenes from an overnight streak culture on a Tryptic Soy Agar plate was inoculated into 10 mL of Tryptic Soy Broth and incubated at 37° C. in a shaker incubator (INNOVA44 from New Brunswick Scientific) for 18 to 20 hours. The resulting bacterial stock containing approximately $1 \times 10^9$ CFU/mL was serially diluted in Butterfield's buffer to obtain an approximately $1 \times 10^6$ CFU/mL inoculum (L. monocytogenes suspension), which was inoculated in the blended ground beef sample to obtain a "spiked beef sample" at approximately $1 \times 10^5$ CFU/mL.

Example 8

A 14 millimeter diameter porous article disk was die punched from the porous article Example 1 and placed into a 13 mm SWINNEX holder (purchased from Millipore (Waltham, Mass., USA). An O-ring seal was used to prevent leakage on the upstream side. The porous article disk was placed on top of the support screen, an O ring was added on top of the porous article disk, and the holder was closed.

The porous article was tested in duplicates. A 1 mL volume of the spiked ground beef was filtered through the porous article disks using a syringe.

Filtrates were collected in 1.5 mL sterile polypropylene microfuge tubes containing 1 mL Butterfield's buffer. A 100 microliter volume from these tubes was added to 900 microliters Butterfield's buffer to obtain a 1:10 dilution. A pre-filtration sample (spiked beef sample) was diluted once more to obtain a 1:100 diluted pre-filtration sample. A 100 microliter volume from each dilution was spread plated on MOX agar plates. The plates were incubated at 37° C. for 18-20 hours and manually analyzed for colony counts. The pre-filtration sample had an average colony count of $52 \times 10^3$ CFU/mL.

The disk turned black indicating the growth of the captured L. monocytogenes. Ground beef samples that were not spiked were plated and had a background flora level of about 4 CFUs/ml.

Capture efficiency was calculated based on colony counts obtained from the plated filtrate and plated pre-filtration sample by using Equations B and C above. The results for % Capture are in Table 5.

Comparative Example 3

A disk 14 mm in diameter was die punched from the fibrous porous matrix of Comparative Example 1 and used for filtration of 1 mL spiked ground beef using a syringe. The filtrates were tested in duplicates as described for Example 8. The results for % Capture are in Table 5. The disk turned black indicating the growth of the captured *L. monocytogenes*.

TABLE 5

Efficiency of removal of *L. monocytogenes* from ground beef

| Filtration Example # | Porous Article or Matrix Example # | % Capture |
|---|---|---|
| 8 | 2 | 55* |
| CE-3 | CE-1 | 24 |

*The standard deviation was 13%.

What is claimed is:

1. A porous article comprising:
   a) porous polymeric particles, wherein the porous polymeric particles comprise a polymerized product of a reaction mixture comprising
      i) a monomer composition consisting essentially of
         (a) 10 to 90 weight percent of a first monomer of Formula (I)

$$CH_2=C(R^1)-(CO)-O[-CH_2-CH_2-O]_p-(CO)-C(R^1)=CH_2 \quad (I)$$

based on a total weight of the monomer composition, wherein p is an integer equal to at least 1 and $R^1$ is hydrogen or alkyl; and
         (b) 10 to 90 weight percent of a second monomer of Formula (III), Formula (IV), or a mixture thereof $$CH_2=CR^1-(CO)-O-Y-R^2 \quad (III)$$

$$CH_2=CR^1-(CO)-O-R^3 \quad (IV)$$

based on the total weight of the monomer composition, wherein
         $R^1$ is hydrogen or methyl;
         Y is a single bond, alkylene, oxyalkylene, or poly(oxyalkylene);
         $R^2$ is a carbocyclic group or heterocyclic group;
         $R^3$ is a linear or branched alkyl; and
      ii) a poly(propylene glycol) having a weight average molecular weight of at least 500 grams/mole, wherein the poly(propylene glycol) is removed from the polymerized product to provide the porous polymeric particles; and
   b) a fibrous porous matrix comprising a mixture of hydrophobic and hydrophilic polymeric fibers, wherein the porous polymeric particles are distributed throughout the fibrous porous matrix.

2. The porous article of claim 1, wherein the fibrous porous matrix comprises nonwoven fibers.

3. The porous article of claim 1, wherein the monomer composition further comprises a second monomer having one (meth)acryloyl group.

4. The porous article of claim 1, wherein the fibrous porous matrix comprises polymeric fibers selected from polyamides, polyolefins, and polysulfones.

5. The porous article of claim 1, wherein the porous article comprises 10 to 55 weight percent porous polymeric particles based on a total dried weight of the porous article and 45 to 90 weight percent fibrous porous matrix based on the total dried weight of the porous article.

6. The porous article of claim 1, wherein the fibrous porous matrix is a nonwoven fibrous layer and further comprises inorganic fibers.

7. The porous article of claim 1, wherein the second monomer is of Formula (III).

8. A separation device comprising:
   a) a container having an inlet and an outlet for passage of a fluid stream through the container; and
   b) a porous article of claim 1 positioned within the container.

9. A system comprising:
   a) a separation device comprising
      i) a container having an inlet and an outlet; and
      ii) a porous article of claim 1 positioned within the container; and
   b) a fluid stream passing through the separation device, wherein the fluid stream enters the inlet and exits the outlet of the container and contacts the porous article positioned within the container.

10. The system of claim 9, wherein the fluid stream comprises a target material and wherein the porous article removes the target material from the fluid stream.

11. The system of claim 10, wherein the target material comprises a microorganism.

12. The system of claim 9, wherein the fluid stream further comprises a lipid.

13. A method of separating a target material, the method comprising:
   a) providing a separation device comprising
      i) a container having an inlet and an outlet; and
      ii) a porous article of claim 1 positioned within the container; and
   b) passing a fluid stream comprising a target material through the separation device, wherein the fluid stream enters the inlet and exits the outlet of the container and contacts the porous article positioned within the container;
   c) removing the target material from the fluid stream, wherein the target material is bound or captured by the porous article.

14. The method of claim 13, wherein the target material comprises a microorganism.

15. The method of claim 14, wherein the microorganism is viable after being bound or captured by the porous article.

16. The method of claim 14, further comprising detecting the amount of microorganism bound or captured by the porous article.

17. The method of claim 13, wherein removing the target material purifies the fluid stream.

18. A method of making a porous article, the method comprising:
   a) providing a plurality of porous polymeric particles, wherein the porous polymeric particles comprise a polymerized product of a reaction mixture comprising
      i) a monomer composition consisting essentially of
         (a) 10 to 90 weight percent of a monomer of Formula (I)

$$CH_2=C(R^1)-(CO)-O[-CH_2-CH_2-O]_p-(CO)-C(R^1)=CH_2 \quad (I)$$

based on a total weight of the monomer composition, wherein p is an integer equal to at least 1 and $R^1$ is hydrogen or alkyl; and (b) 10 to 90 weight percent of a second monomer of Formula (III), Formula (IV), or a mixture thereof $$CH_2=CR^1-(CO)-O-Y-R^2 \qquad (III)$$

$$CH_2=CR^1-(CO)-O-R^3 \qquad (V)$$

based on the total weight of the monomer composition, wherein $R^1$ is hydrogen or methyl;

Y is a single bond, alkylene, oxyalkylene, or poly(oxyalkylene);

$R^2$ is a carbocyclic group or heterocyclic group;

$R^3$ is a linear or branched alkyl; and ii) a poly(propylene glycol) having a weight average molecular weight of at least 500 grams/mole, wherein the poly(propylene glycol) is removed from the polymerized product to provide the porous polymeric particles; and b) distributing the porous polymeric particle throughout a fibrous porous matrix comprising a mixture of hydrophobic and hydrophilic polymeric fibers.

19. The method of claim 18, wherein the porous article comprises 10 to 55 weight percent porous polymeric particles based on a total dried weight of the porous article and 45 to 90 weight percent fibrous porous matrix based on the total dried weight of the porous article.

* * * * *